(12) United States Patent
Tsai et al.

(10) Patent No.: US 11,779,616 B1
(45) Date of Patent: Oct. 10, 2023

(54) METHOD OF IMPROVING MEMORY AND LEARNING ABILITY

(71) Applicant: GENMONT BIOTECH INC., Tainan (TW)

(72) Inventors: Wan-hua Tsai, Kaohsiung (TW); I-ling Hsu, Tainan (TW); Chih-ho Lai, New Taipei (TW); Chia-lin Wu, Taipei (TW)

(73) Assignee: GENMONT BIOTECH INC., Tainan (TW)

( * ) Notice: Subject to any disclaimer, the term of this patent is extended or adjusted under 35 U.S.C. 154(b) by 0 days.

(21) Appl. No.: 17/818,977

(22) Filed: Aug. 11, 2022

(30) Foreign Application Priority Data

May 9, 2022 (TW) .................................. 111117381

(51) Int. Cl.
*A61K 35/747* (2015.01)
*A61P 25/28* (2006.01)

(52) U.S. Cl.
CPC ............ *A61K 35/747* (2013.01); *A61P 25/28* (2018.01)

(58) Field of Classification Search
None
See application file for complete search history.

(56) References Cited

U.S. PATENT DOCUMENTS

| 10,456,430 B1 * | 10/2019 | Chen | A61P 31/04 |
| 10,638,784 B2 * | 5/2020 | Chen | A61P 1/04 |
| 2017/0368135 A1 * | 12/2017 | Davey | A61K 36/28 |

OTHER PUBLICATIONS

Naomi et al. "Probiotics for Alzheimer's disease: a systematic review". Nutrients. 2022, 14, 20, pp. 1-24, published Dec. 22, 2021.*

* cited by examiner

*Primary Examiner* — Vera Afremova
(74) *Attorney, Agent, or Firm* — PV IP PC; Wei Te Chung; Zhigang Ma

(57) ABSTRACT

A probiotic composition of improving memory and learning ability is disclosed. The probiotic composition comprises *Lactobacillus acidophilus* GMNL-185 and *Lactobacillus rhamnosus* GMNL-680, wherein the *Lactobacillus acidophilus* GMNL-185 was deposited in the China Center for Type Culture Collection in Wuhan, China on Nov. 3, 2017 under an accession number CCTCC NO. M 2017764, and the *Lactobacillus rhamnosus* GMNL-680 was deposited in the China Center for Type Culture Collection in Wuhan, China on Nov. 3, 2017 under an accession number CCTCC NO. M 2017766, wherein a ratio of a number of bacteria of the *Lactobacillus acidophilus* GMNL-185 to a number of bacteria of the *Lactobacillus rhamnosus* GMNL-680 is 1:1.

1 Claim, 28 Drawing Sheets

Specification includes a Sequence Listing.

METHOD OF IMPROVING MEMORY AND LEARNING ABILITY

CROSS-REFERENCE TO RELATED APPLICATIONS

The present application claims the benefit of Taiwan patent serial number 111117381 filed May 9, 2022, the disclosure of which is incorporated herein by reference. The official copy of sequence listing is submitted concurrently with the specification as an XML file with a file name of TP220022-US SEQUENCELIST F.xml, a creation date of Aug. 10, 2022 and a size of 6738 bytes. This sequence listing is part of the specification and is hereby incorporated in its entirely by reference herein.

FIELD OF INVENTION

The present disclosure relates to a probiotic composition of *Lactobacillus acidophilus* and *Lactobacillus rhamnosus*, and in particular to a probiotic composition of *Lactobacillus acidophilus* GMNL-185 and *Lactobacillus rhamnosus* GMNL-680 of improving memory and learning ability and use thereof.

BACKGROUND OF INVENTION

In addition to preventing or improving allergy, urinary tract infection, metabolism and other diseases, probiotics can affect nerves, neuroendocrine, and neuroimmunity by various ways, thereby promoting effects on a central nervous system. The main ways are shown as follows: (1) promoting fermentation and absorption of complex carbohydrates, so as to produce short-chain fatty acids; (2) producing vitamin B and vitamin K; (3) competing with pathogenic bacteria to adsorb to intestines; (4) promoting growth of probiotics; (5) inhibiting growth of intestinal pathogenic bacteria (6) maintaining integrity of an intestinal barrier; (7) modulating host immune response, reducing chronic inflammation; and (8) promoting productions of gamma-aminobutyric acid (neurotransmitters), serotonin, acetylcholine, histamine, short-chain fatty acids, and dopamine. In addition, studies show that probiotics can improve stress-related disorders such as anxiety, autism, depression, schizophrenia, and dementia.

Studies show that fluoride causes memory impairment in mice, and decreases in relative abundance of Firmicutes and *Lactobacillus* belonging to the phylum of Firmicutes in the gut microbiota of mice. However, oral administration of *Lactobacillus johnsonii* BS15 can improve memory ability of mice and restore a number of Firmicutes and *Lactobacillus*. New evidences from 16S rRNA gene sequencing of gut microbiota of Collaborative Cross mice show that the higher the relative abundance of *Lactobacillus* in the gut microbiota is, the higher the memory potential is. In addition, the concentration of brain lactic acid in and memory of germ-free mice are significantly improved after feeding *Lactobacillus*.

Studies further show that there are fewer Firmicutes, *Actinobacteria*, SMB53, *Dialister, Clostridium, Turicibacter*, and cc115 (family Erysipelotrichaceae) in intestines of Alzheimer's patients. These bacteria are highly associated with pathological markers of cerebrospinal fluid of Alzheimer's disease, such as Aβ42/Aβ40, p-tau, p-tau/Aβ42. As mentioned above, gut microbiota can interact with the brain through a gut—brain axis, affecting abilities of emotion, behavior, cognition, and memory.

SUMMARY OF INVENTION

Technical Problems

A main purpose of the present disclosure is to provide a probiotic composition and use thereof, which can improve memory and learning ability and use thereof.

Technical Solutions

In order to achieve the foregoing purpose of the present disclosure, the present disclosure provides a probiotic composition of improving memory and learning ability, comprising: *Lactobacillus acidophilus* GMNL-185 and *Lactobacillus rhamnosus* GMNL-680, wherein the *Lactobacillus acidophilus* GMNL-185 was deposited in the China Center for Type Culture Collection in Wuhan, China on Nov. 3, 2017 under an accession number CCTCC NO. M 2017764, and the *Lactobacillus rhamnosus* GMNL-680 was deposited in the China Center for Type Culture Collection in Wuhan, China on Nov. 3, 2017 under an accession number CCTCC NO. M 2017766, and a ratio of a number of bacteria of the *Lactobacillus acidophilus* GMNL-185 to a number of bacteria of the *Lactobacillus rhamnosus* GMNL-680 is 1:1.

In order to achieve the foregoing purpose of the present disclosure, the present disclosure further provides a method of improving memory and learning ability, comprising: administering the probiotic composition as mentioned above to a subject who needs to improve memory or learning ability.

Beneficial Effects

After the probiotic composition of the present disclosure is administrated, the probiotic composition can colonize and grow within the gut of an individual. Moreover, the probiotic composition can change the microbial composition of the individual, and increase relative abundance of Firmicutes, *Lactobacillus*, and *Pediococcus* in the gut, thereby changing a neural activity of specific neural regions in a brain and strength of memory traces, so as to achieve an effect of enhancing memory and learning ability of the individual.

DESCRIPTION OF DRAWINGS

In order to more clearly illustrate the above contents of the present disclosure, the following is a detailed description of the preferred embodiments with reference to the accompanying drawings:

FIG. 8A and FIG. 8B show effects of relative abundance at the phylum level of gut microbiota of fruit flies, wherein FIG. 8A shows individual changes of 3 repeats, and FIG. 8B shows average changes.

FIG. 9A and FIG. 9B show effects of relative abundance at the genus level of gut microbiota of fruit flies, wherein FIG. 9A shows individual changes of 3 repeats, and FIG. 9B shows average changes.

DETAILED DESCRIPTION OF PREFERRED EMBODIMENTS

Figure 1A:
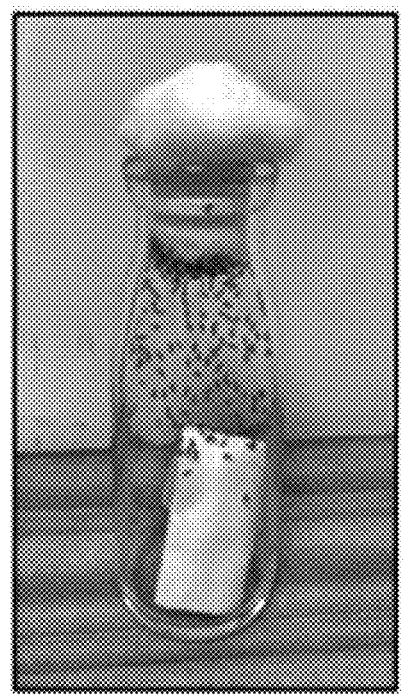
FIG. 1A to FIG. 1G respectively show a *Drosophila melanogaster* (fruit fly) learning machine, T-maze, and introduction of an olfactory memory assay process.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As used herein, the singular form "a", "an" and "the" include plural references unless the context clearly dictates otherwise. The numerical range (such as 10% to 11% of A) includes the upper and lower limits (i.e., 10%≤A≤11%) unless otherwise specified. If the numerical range does not define the lower limit (such as less than 0.2% of B, or below 0.2% of B), it means that the lower limit may be 0 (i.e., 0%≤B≤0.2%). The above terms are made for the purposes of describing and illustrating the present disclosure and should not be taken in a limiting sense.

The present disclosure provides a probiotic composition of improving memory and learning ability, comprising: *Lactobacillus acidophilus* GMNL-185 (hereinafter called GMNL-185) and *Lactobacillus rhamnosus* GMNL-680 (hereinafter called GMNL-680), wherein the GMNL-185 was deposited in the China Center for Type Culture Collection in Wuhan, China on Nov. 3, 2017 under an accession number CCTCC NO. M 2017764, and the GMNL-680 was deposited in the China Center for Type Culture Collection in Wuhan, China on Nov. 3, 2017 under an accession number CCTCC NO. M 2017766, and a ratio of a number of bacteria of the GMNL-185 to a number of bacteria of the GMNL-680 is 1:1.

The probiotic composition of the present disclosure may further comprise a pharmaceutically acceptable carrier. The pharmaceutically acceptable carrier may include one or more agents selected from the group consisting of solvents, stabilizers, emulsifiers, suspending agents, decomposing agents, flavoring agents, binding agents, excipients, cosolvents, chelating agents, diluents, gelling agents, preservatives, lubricants and surfactants.

The term "administer" the composition to a subject refers to directly administering the composition to the subject, and the composition can be administered by professional medical personnel, or on the subject's own.

Generally, the "subject" is human. However, in other embodiments, the "subject" may be a non-human mammal, such as a non-human primate, dog, cat, cow, horse, rabbit, pig, etc. In the embodiment of the present disclosure, the "subject" treated by the probiotic composition of the present disclosure is *Drosophila melanogaster* (fruit fly). Certainly, the present disclosure is not limited to this. In other embodiments, the "subject" treated by the probiotic composition herein may be, for example, animals commonly used for screening, characterizing and evaluating compositions (compounds, drugs, probiotics) and treatments.

The term "treatment" refers to methods used to obtain beneficial or desired results (including clinical results). For the purpose of the present disclosure, beneficial or desired clinical results include, but are not limited to, reduction or improvement of one or more symptoms, reduction of the disease degree, stability of the disease state (i.e., no deterioration), prevention of the disease spread, delay or slowing of the disease progress, and improvement, alleviation and remission (partial or complete remission) of the disease state.

The probiotic composition of the present disclosure can be prepared into a variety of dosage forms, including but not limited to: solutions, emulsions, suspensions, powders, pastilles, pills, lozenges, tablets, chewing gums, capsules, and other dosage forms similar to or applicable to the probiotic composition of the present disclosure.

Evaluation and Identification of Strains

Characteristics of GMNL-185

The source of the GMNL-185 is the human small intestine.

The physiological characteristics of GMNL-185 are shown as follows. The GMNL-185 are gram-positive, catalase-negative, oxidase-negative, motility-negative, and non-endospore forming bacteria. Colonial morphology: intact edges, with an average size of 1.5 mm×1.5 mm, transparent, with a smooth bulge. Culturing temperature: 35° C. to 40° C. Culturing pH: 4.0 to 7.0. Oxygen effect: facultative anaerobic.

In addition, after the genomic DNA of the GMNL-185 was extracted, the partial sequence of the 16S rRNA gene was amplified by the primer pairs shown as SEQ ID NO: 1 and SEQ ID NO: 2, wherein the forward primer is PAF primer, and the downstream primer is 536R primer. The obtained nucleic acid fragment is shown as SEQ ID NO: 3. The method for extracting genomic DNA is well known to those with ordinary knowledge in the technical field of the present disclosure, and will not be described here.

The nucleic acid fragment has more than 99% sequence identity compared with the 16S rRNA gene sequence of four Lactobacillus acidophilus (GenBank numbers: NR_117812.1, NR_113638.1, NR_117062.1, and NR_043182.1) in the GenBank of National Center for Biotechnology Information (NCBI). Thus, the nucleic acid fragment is confirmed as *Lactobacillus acidophilus*.

SEQ ID NO: 1 及 SEQ ID NO: 2:

TABLE 1

| Primer | Sequence ID number | Primer sequence |
|---|---|---|
| PAF | SEQ ID NO: 1 | AGA GTT TGA TCC TGG CTC AG |
| 536R | SEQ ID NO: 2 | GTA TTA CCG CGG CTG CTG |

Characteristics of GMNL-680

The source of GMNL-680 is the human vagina.

The physiological characteristics of the GMNL-680 are shown as follows. The GMNL-680 are gram-positive, catalase-negative, oxidase-negative, motility-negative, and non-endospore forming bacteria. Colonial morphology: intact edges, with an average size of 2.5 mm×2.5 mm, milky white, with a smooth bulge. Culturing temperature: 35° C. to 40° C. Culturing pH: 4.0 to 7.0. Oxygen effect: facultative anaerobic.

In addition, after the genomic DNA of GMNL-680 was extracted, the partial sequence of the 16S rRNA gene was amplified by the primer pairs shown as SEQ ID NO: 1 and SEQ ID NO: 2 as shown in the table 1. The obtained nucleic acid fragment is shown as SEQ ID NO: 4. The method for extracting genomic DNA is well known to those with ordinary knowledge in the technical field of the present disclosure, and will not be described here.

The effects of the probiotic composition of GMNL-185 and GMNL-680 in improving learning ability and memory ability were evaluated by using a *Drosophila melanogaster* (fruit fly) animal model.

In the following experiments, the experimental methods without specific conditions are selected according to conventional methods and conditions, or according to the instructions of the kit.

Experimental Method

Feeding Method of Lactic Acid Bacteria for Young and Aged Fruit Flies (*Drosophila melanogaster*)

*Canton-S* strain (wild-type) of *Drosophila melanogaster* was used in the present experiment. The fruit flies were fed on *Drosophila* growth medium prepared by cornmeal and agar, maintaining on a 12-hour light/12-hour dark cycle at a constant temperature of 24° C. and a humidity of 50%. There are two methods to prepare the lactic acid bacteria medium for the fruit flies: (1) 100 μl of the lactic acid bacteria ($1 \times 10^8$ CFU/ml) after twice subculture was added into the common medium of the lactic acid bacteria and the fruit flies (25% *Lactobacillus* MRS broth +75% cornmeal medium for fruit flies), and the lactic acid bacteria were incubated at 37° C. for 1 day; (2) Bacterial powder ($3 \times 10^9$ CFU/ml) was added to the common medium of the lactic acid bacteria and the fruit flies (25% *Lactobacillus* and MRS broth +75% cornmeal medium for fruit flies). Then, the fruit flies at 7 days after emergence (young) or 21 days after emergence (aged) were placed in a sealed glass bottle of the above lactic acid bacteria medium for feeding lactic acid bacteria at 25° C. for 5 days. The fruit flies were then removed and subjected to a memory assay.

Analysis of Learning and Memory Ability in Fruit Flies

The experimental concept of Pavlovian conditioning is used in the present experiment. In a fruit fly learning machine (T-maze), an odor combined with an electric shock causes the fruit flies to generate associative learning and memory. This technology is used to screen the degree of improvement of learning and memory ability by specific lactic acid bacteria after the fruit flies were fed the lactic acid bacteria, so as to achieve the basis for evaluating the specific lactic acid bacteria for the improvement of learning and memory ability. In the experiment, 15 strains of lactic acid bacteria were screened (see Table 2), the top two strains of lactic acid bacteria with the best efficacy of enhancing or improving the learning and memory ability of the fruit flies were selected, and the benefits of single strain and a composition of two lactic acid bacteria strains were further compared.

TABLE 2

| Number | species | strain |
|---|---|---|
| A1 | L. rhamnosus | CCTCC M 203098 |
| A2 | L. plantarum | CCTCC M 2017767 |
| A3 | L. paracasei | CCTCC M 204012 |
| A4 | L. rhamnosus | GMNL-680 |
| A5 | L. plantarum | CCTCC M 2017765 |
| A6 | L. fermentum | CCTCC M 204055 |
| A7 | L. plantarum | NITE BP-03510 |
| A8 | L. fermentum | CCTCC M 2016225 |
| A9 | L. plantarum | CCTCC M 2016571 |
| A10 | L. paracasei | CCTCC M 2011331 |
| A11 | L. rhamnosus | CCTCC M 2015610 |
| A12 | L. paracasei | CCTCC M 2016226 |
| A13 | L. reuteri | CCTCC M 207154 |
| A14 | L. acidophilus | GMNL-185 |
| A15 | L. casei | CCTCC M 2013197 |

Figure 1B:
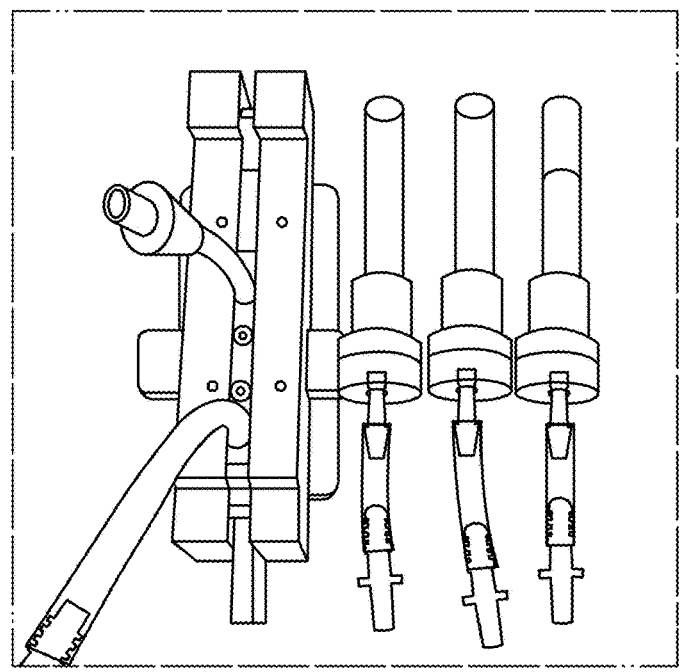
Figure 1C:
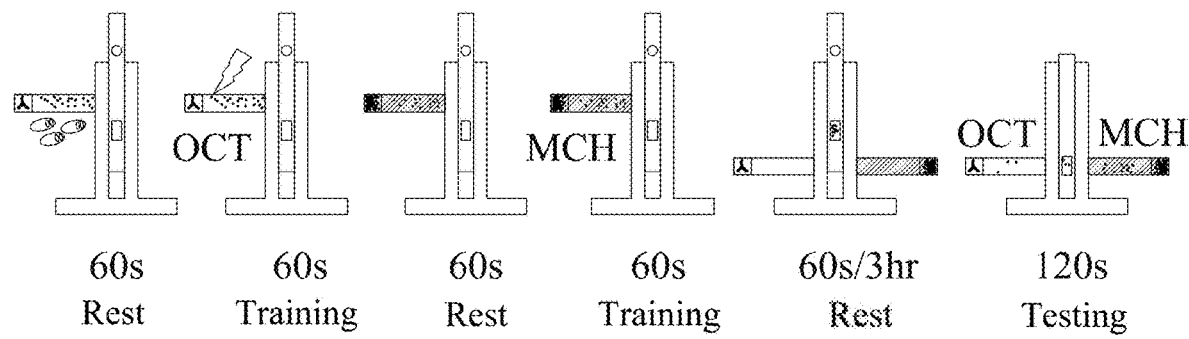
Figure 1D:
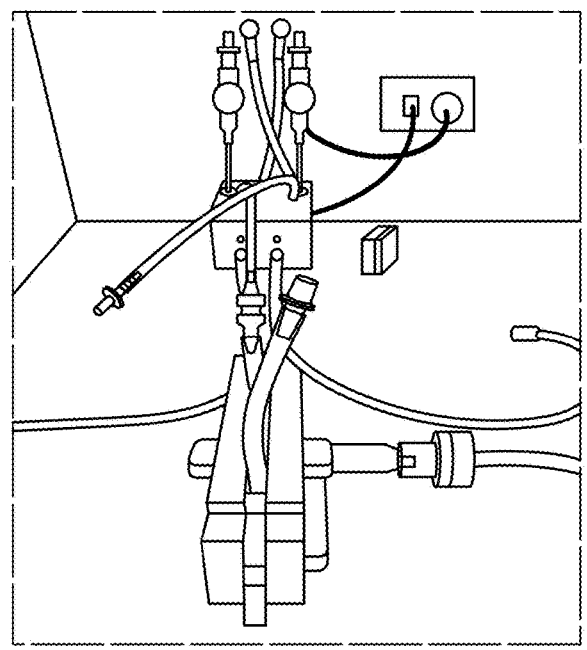
Figure 1E:
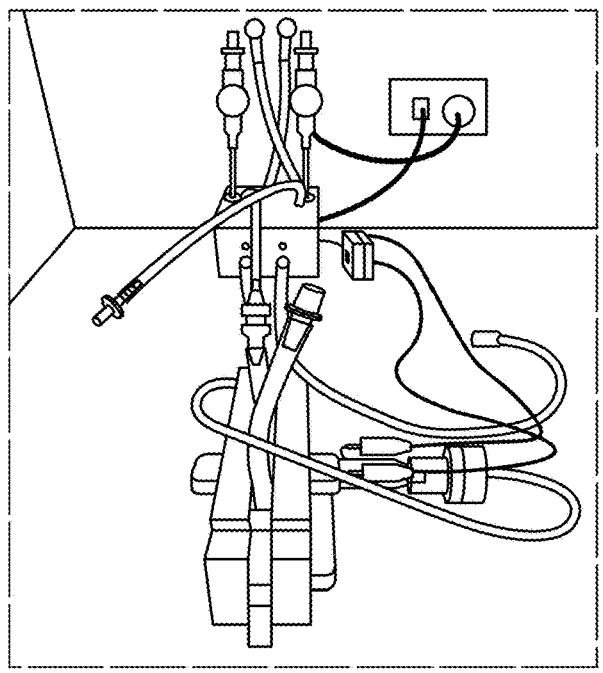
Figure 1F:
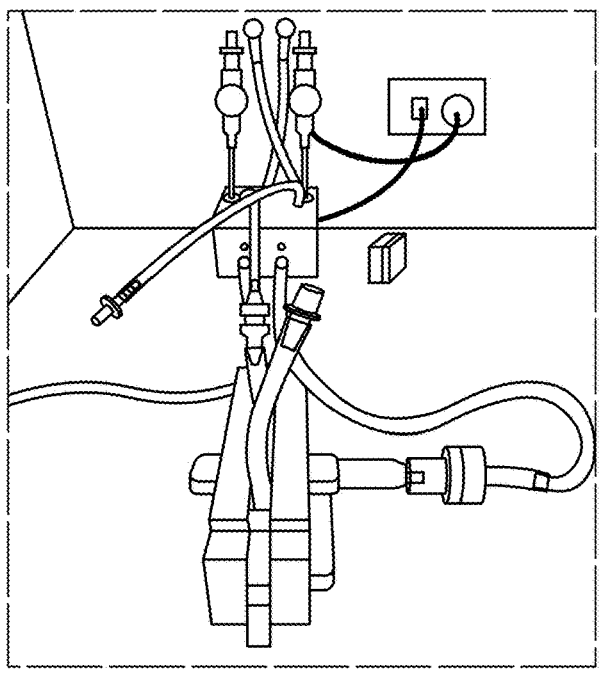
Figure 1G:
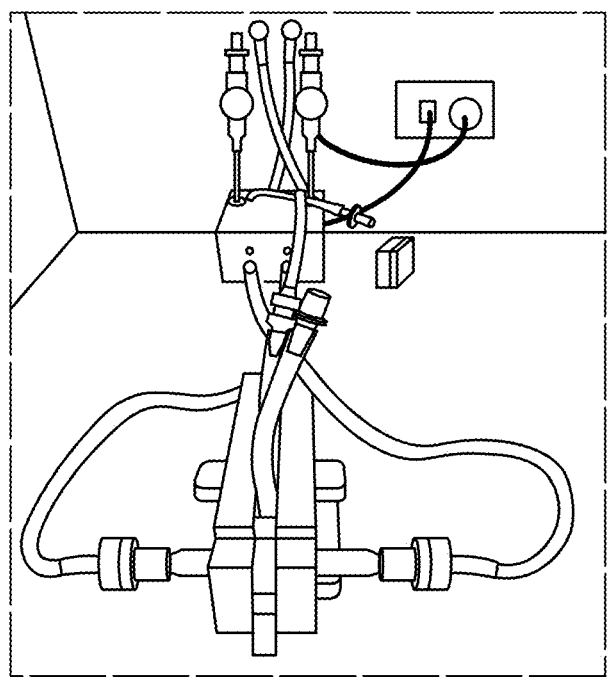
Figure 2A:
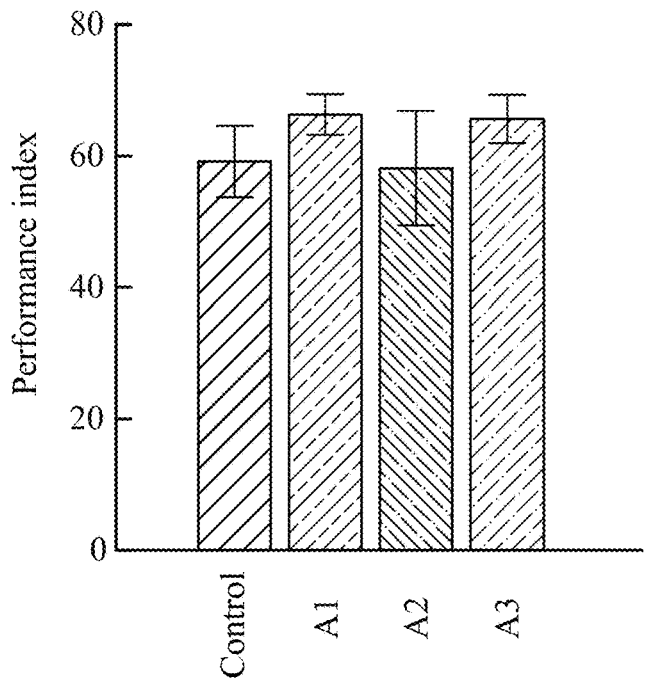
FIG. 2A to FIG. 2E are bar charts respectively showing 3-minute memory ability of young fruit flies after feeding different lactic acid bacteria for 5 days.
Figure 2B:
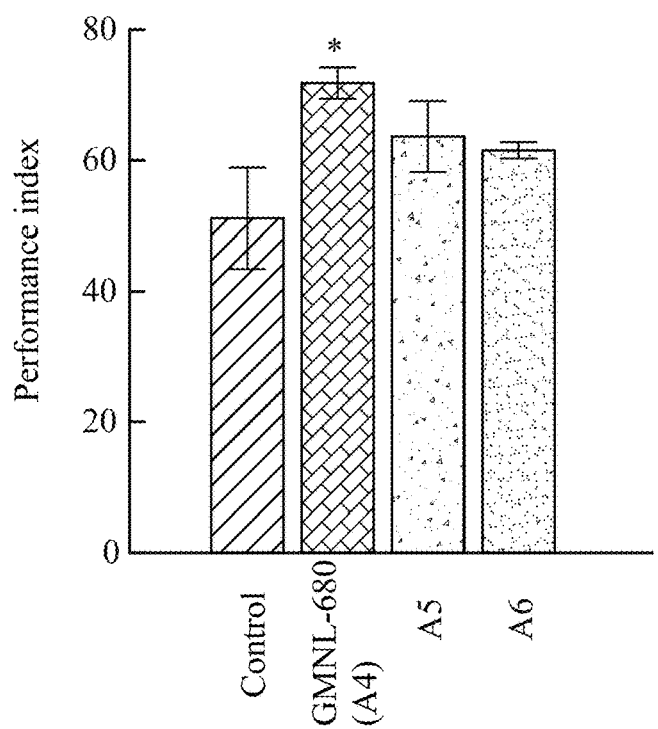
Figure 2C:
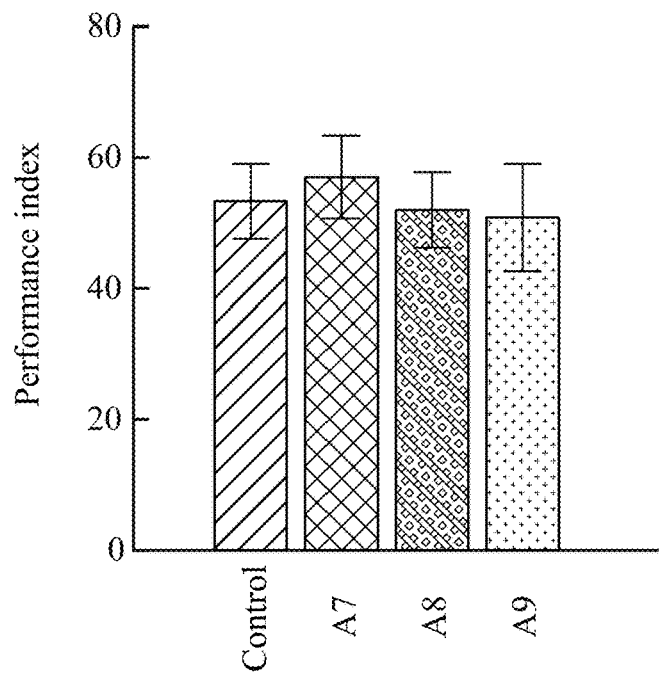
Figure 2D:
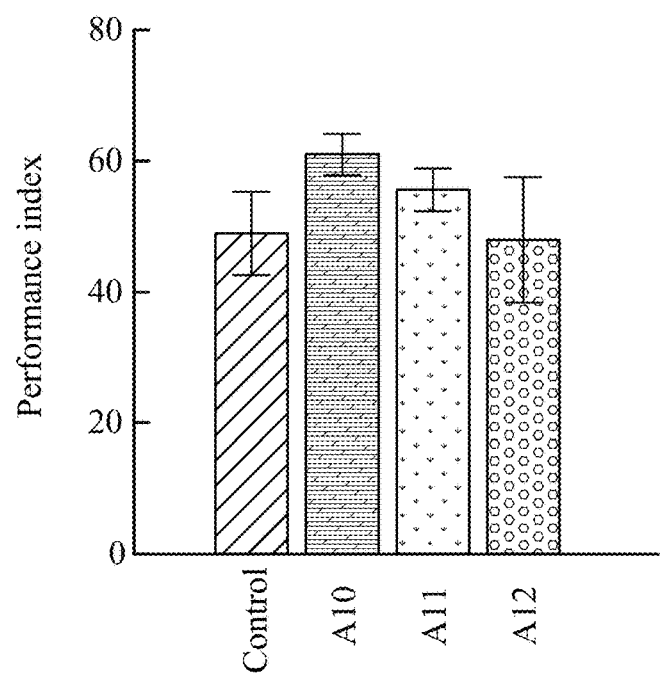
Figure 2E:
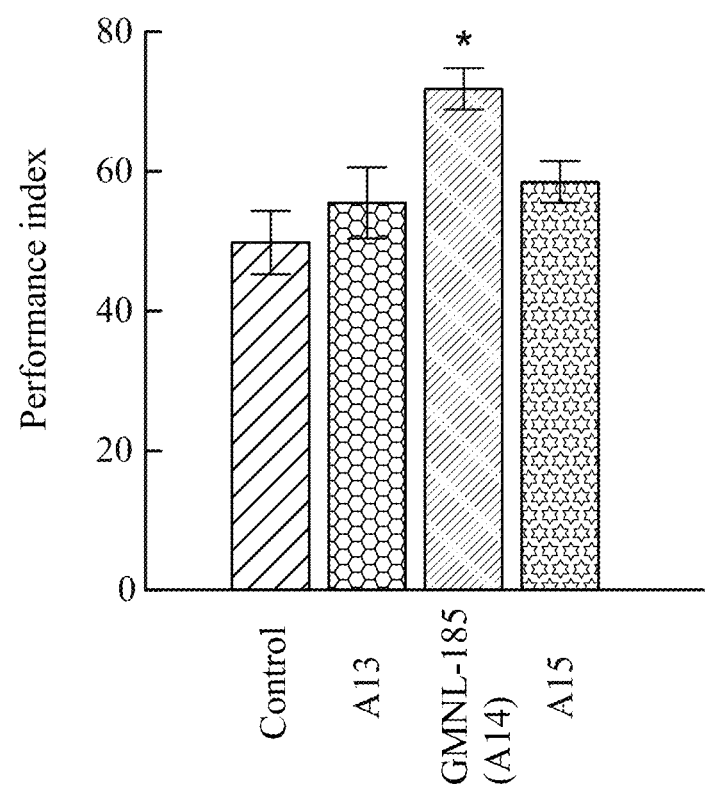

A memory assay for fruit flies includes 3-minute memory assay and 1-hour memory assay, so as to observe establishments of short-term memory and long-term memory in the brain of the fruit fly. In the 3-minute memory assay, the fruit flies were transferred from the medium to an empty vial with Kimwipes wipes (FIG. 1A) for the first 1 hour, and then were placed in a behavioral room with a temperature of 25° C., a humidity of 70%, and a red light. FIG. 1B shows a T-maze, an odor tube, and an electric shock tube from left to right, respectively. At the beginning of the assay, about 50 fruit flies were placed in the electric shock tube to rest for 1 minute (FIG. 1D), and then were exposed to 3-octonal (OCT) odor with electric pulses of 40V for 3 times 1 minute (FIG. 1E), followed by 1 minute rest and ultimately exposure to 4-methylcyclohexanol (MCH) odor for 1 minute in the absence of shocks (FIG. 1F). The fruit flies performing the 3-minute memory assay would be rest for 1 minute after exposure to the second odor (MCH). Then, the trained fruit flies were placed in the T-maze and allowed to choose between two odor tubes (FIG. 1G). After the fruit flies chose the two odors in the T-maze for 2 minutes, the fruit flies distributed in the two odor tubes were collected and a performance index (PI) was calculated, i.e., PIOCT in the present assay (refer to FIG. 1C). After the above assay, a second batch of untrained fruit flies repeated the same steps for the second assay, in which the fruit flies were exposed to MCH in the presence of shocks while exposed to OCT in the absence of shocks. Then, the fruit flies were placed in the T-maze to choose the two odors, followed by a calculation for the second PIMCH value. In this assay, a group of PI values was a result of an average of PIOCT and the PIMCH. The PI value was calculated as follows: the number of fruit flies exposed to the odor without shocks (Unconditioned stimulus, CS−) minus the number of fruit flies exposed to the odor with shocks (Conditioned stimulus, CS+) divided by the total number of fruit flies in the assay. In the 1-hour memory assay, after exposed to a second odor, the fruit flies were transferred to a feeding tube containing fresh food to rest for 3 hours, and then transferred to a T-maze for two odor choices for 2 minutes, followed by collection of fruit flies to calculate a PI value. The higher the PI value is, the better the learning and memory performance of fruit flies is.

Effect of Lactic Acid Bacteria on Neural Activity of Mushroom Bodies in Fruit Flies In fruit flies, learning and memory mainly rely on "mushroom" neurons in a brain. In order to understand whether feeding lactic acid bacteria changes neural activity in a brain of a fruit fly, thereby enhancing learning and memory, calcium imaging was used to observe neural activity of a mushroom body of a live *Drosophila* brain. Specifically, GCaMP6 protein is a protein that can detect calcium ion concentration. GCaMP6 itself is a green fluorescent protein. When GCaMP6 is combined with environmental calcium ions, its protein structure changes, resulting in changes in green fluorescence intensity. When a nerve cell emits an action potential, a large amount calcium ions enter the nerve cell through calcium ion channels. Therefore, changes in fluorescence intensity can be observed under a microscope to understand the calcium ion concentration in the living *Drosophila* brain by genetically expressing the GCaMP6 protein in *Drosophila* mushroom body neurons, thereby quantifying activation of nerve cells after receiving external stimuli. The GAL4 *Drosophila melanogaste* strain (R13F02-GAL4) was used to mate with the UAS-GCaMP6 *Drosophila melanogaste*, and their offsprings were taken and fed lactic acid bacteria to observe whether mushroom body neurons of the fruit flies with or without feeding lactic acid bacteria respond to external odor stimuli, so as to understand whether lactic acid bacteria in the guts affect neural activity of the mushroom body in the brain.

Use of Gene Transfer Technique to Express Fluorescent Protein in Lactic Acid Bacteria Lactic acid bacteria were cultured in MRS broth containing 5% threonine overnight, and then the bacterial solution was diluted 100 times and cultured again to an absorbance value ($OD_{600\,nm}$) of 0.6 to 0.8. The lactic acid bacteria were collected by centrifugation, and then washed 3 times with ice electroporation buffer (0.286 M sucrose, 1 mM $MgCl_2$, 20% glycerol), and finally re-dissolved with the electroporation buffer, dispensed, frozen and stored at −80° C., so as to complete preparation of competent cells of lactic acid bacteria.

The prepared competent cells were mixed with 2 μg plasmid DNA (pTRKH3-ermGFP or pLEM415-IdhL-mRFP1) evenly and transferred to an electroporation tube to conduct electroporation with 2.5 kV, 25 μFD, and 200 Ω. After the electroporation, MRS broth was added and incubated for 3 hours to repair the bacteria. Finally, a suspension of the electroporated cells was spread onto culture plates containing antibiotics and incubated in an anaerobic environment for 2-3 days. Colonies grown on the culture plate were picked up and spread on glass slides, and then the lactic acid bacteria were observed by a confocal microscopy for fluorescent protein expression.

Confirmation of Existence and Growth of Lactic Acid Bacteria Expressing Fluorescent Proteins in Fruit Fly Guts 100 μl of lactic acid bacteria expressing fluorescent protein ($1\times10^8$ CFU/ml) was taken and added into a medium for fruit flies (25% *Lactobacillus* MRS broth +75% cornmeal medium for fruit flies), and incubated at 37° C. for 1 day. The fruit flies were placed in a sealed glass bottle with the above medium to be fed lactic acid bacteria at 25° C. for 5 days. A gut of the fruit fly was dissected and placed on a glass slide, and the gut of the fruit fly was observed by a confocal microscopy for fluorescence performance.

Analysis of Gut Microbiota of Fruit Flies After Feeding Lactic Acid Bacteria

NGS Analysis of Gut Microbiota of Fruit Flies

In the present experiment, 16S rRNA next-generation sequencing was used to analyze gut microbiota of fruit flies. Intestinal tissue of fruit flies was first taken out, and then ground and homogenized using a high-throughput tissue grinder, followed by centrifugation to obtain the gut microbiota in a supernatant. Extraction of the gut microbiota DNA was performed using QIAamp fast DNA tissue kit according to a standard operating manual. A concentration of the extracted DNA was detected by a micro-volume spectrophotometer, in which a ratio of $OD_{260}$ to $OD_{280}$ must range from 1.7 to 2.2, and a concentration of the DNA must be more than 50 ng/μL, and the sample was diluted to 4 to 6 ng/μL using the Elution buffer provided in the kit for subsequent 16S rRNA analysis. Variable region 3 and variable region 4 (V3-V4) of 16S rRNA were amplified by KAPA HiFi DNA polymerase, and then the amplified DNA was purified using KAPA pure beads. The quality of the purified DNA was confirmed by capillary electrophoresis and fluorescence spectroscopy. The purified DNA was amplified for the second time and a DNA database was established. PCR products obtained from the second amplification were purified by KAPA pure beads again, and the quality and concentration were confirmed by capillary electrophoresis and fluorescence spectroscopy. The labeled and established DNA at a final concentration of 4 nM was mixed with 20% viral DNA, followed by 16S rRNA sequencing analysis using the MiSeq v3 (600 cycle) kit.

Bioinformatics Analysis

The FASTQ files obtained after next-generation sequencing were analyzed using QIIME2 software, and DADA2 was used to filter out DNA fragments smaller than 400 bp. Compared with the Greengenes v13.8 database, the sequences were divided into different operational taxonomic units (OUT) according to a similarity threshold of 97%, and an operational unit table (OTU table) was established. The LEfSe (Linear discriminant analysis (LDA) effect size) online software was used to analyze main microorganisms among the groups, and a LDA score greater than 2 was regarded as the core flora with significant differences. In all analyses, a p-value less than 0.05 was considered statistically significant.

Experimental Results

Effect of Lactic Acid Bacteria on the Learning and Memory Ability of Fruit Flies

Short-Term and Long-Term Memory of Young Fruit Flies

A memory assay was carried out using a method of fruit fly olfactory learning and memory. The memory ability of young fruit flies at 7 days after emergence after 5 days with or without feeding lactic acid bacteria for 5 consecutive days was compared. A 3-minute memory assay was initially used to screen 15 strains of lactic acid bacteria for their ability to improve memory of young fruit flies (FIG. 2A to FIG. 2E). The results showed that GMNL-680 (i.e., A4) (FIG. 2B) and GMNL-185 (i.e., A14) (FIG. 2E) have the best efficacy of enhancing memory of the young fruit flies.

Figure 3A:
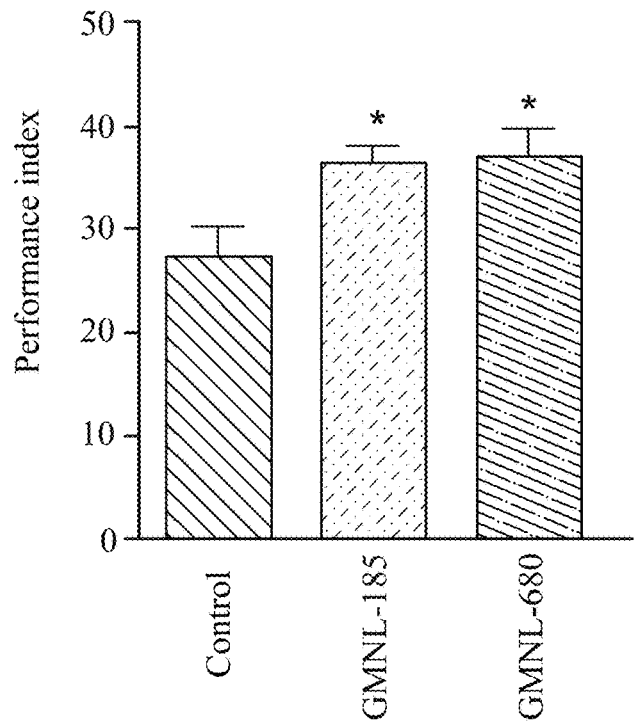
FIG. 3A to FIG. 3D are bar charts respectively showing learning and memory ability of young fruit flies after feeding *Lactobacillus acidophilus* GMNL-185 (hereinafter called GMNL-185) and *Lactobacillus rhamnosus* GMNL-680 (hereinafter called GMNL-680) for 5 days.
Figure 3B:
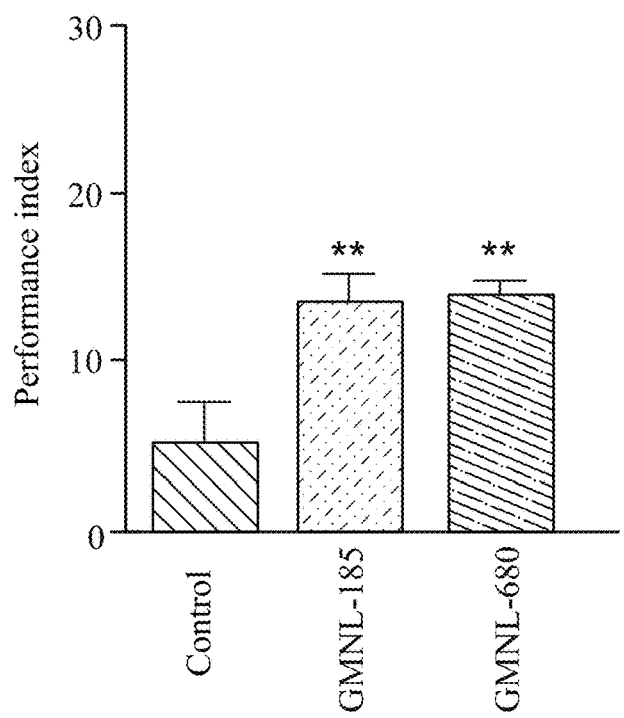
Figure 3C:
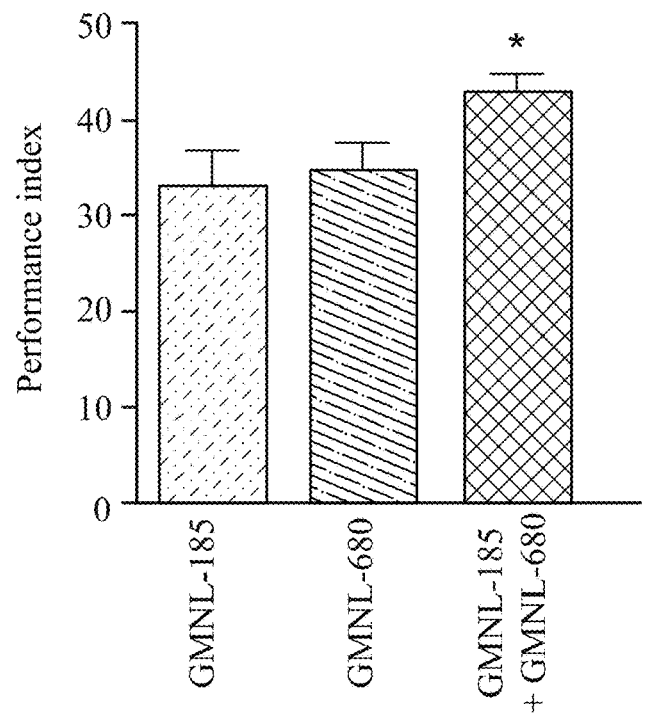
Figure 3D:
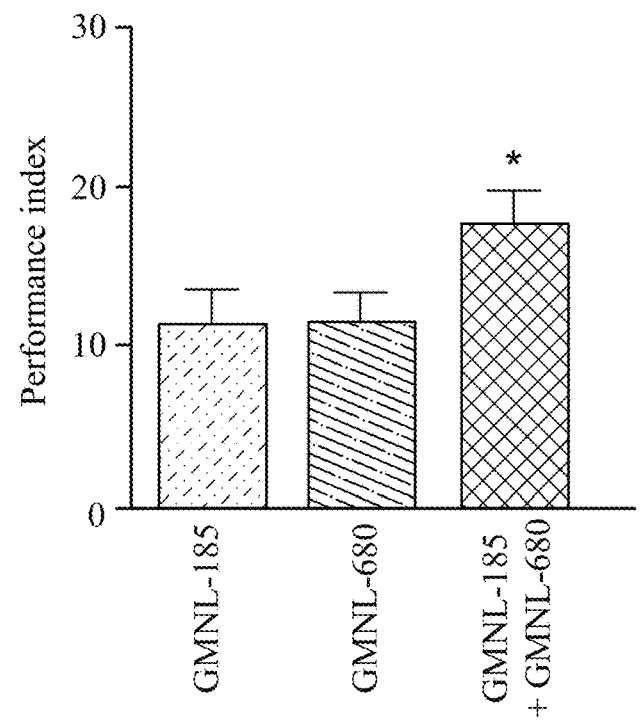

Effects of GMNL-185, GMNL-680, and a lactic acid bacteria composition (i.e., the probiotic composition of the present disclosure, with the ratio of 1:1) on short-term (3 minutes) memory ability and long-term (1 hour) memory ability of the fruit flies were further analyzed. The results of fruit fly memory assays showed that the 3-minute and 1-hour memory of the young fruit flies fed GMNL-185 or GMNL-680 alone were significantly higher than those of the group that were fed lactic acid bacteria (FIG. 3A and FIG. 3B). The composition of GMNL-185 and GMNL-680 was further analyzed for an improved and synergistic effect. The results showed that the 3-minute memory (FIG. 3C) and the 1-hour memory (FIG. 3D) of the young fruit flies fed the composition of GMNL-185 and GMNL-680 were significantly better than those of the groups fed GMNL-185 or GMNL-680 alone. The above results show that the short-term and long-term memory ability of the fruit flies can be effectively improved by GMNL-185, GMNL-680 and the composition thereof, in which the composition of GMNL-185 and GMNL-680 (i.e., the probiotic composition of the present disclosure, with the ratio of 1:1) has the best effectiveness.

Short-Term Memory and Long-Term Memory in the Aged Fruit Flies

Figure 4A:
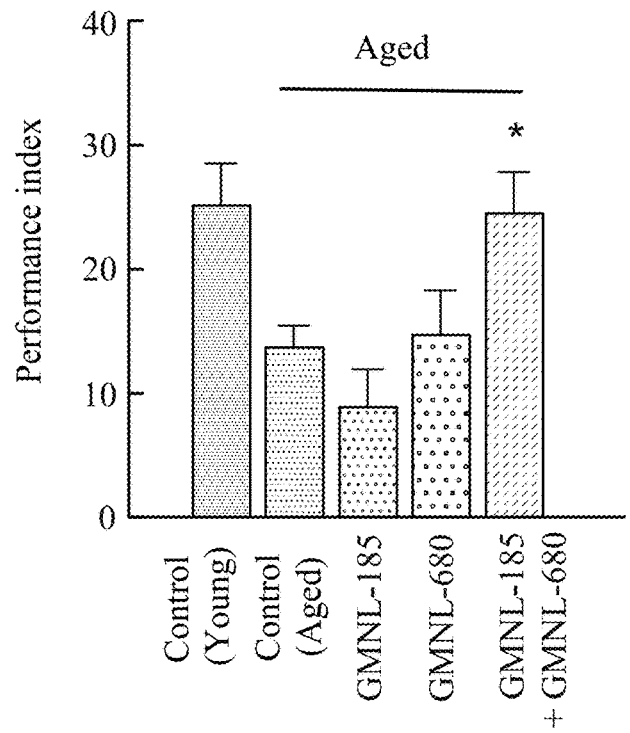
FIG. 4A and FIG. 4B are bar charts respectively showing learning and memory ability of aged fruit flies after feeding GMNL-185, GMNL-680, and a combination of GMNL-185 and GMNL-680 for 5 days.
Figure 4B:
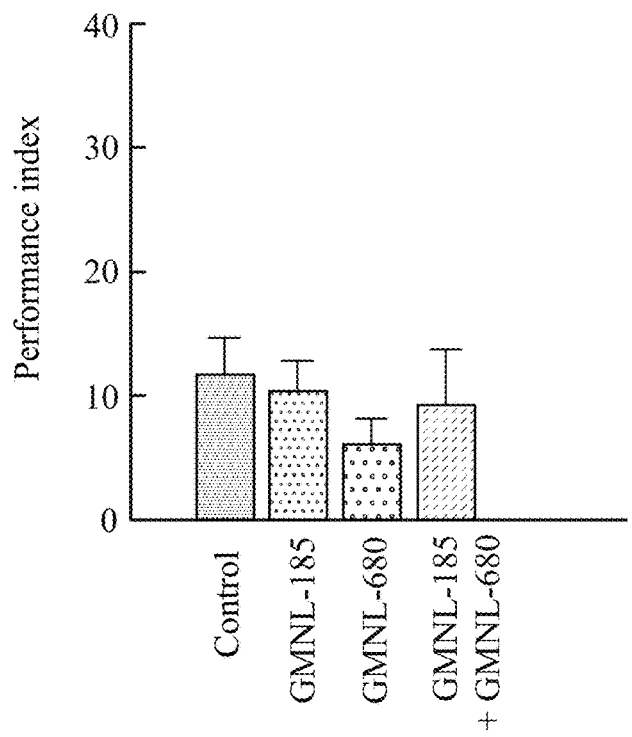

In order to understand whether feeding lactic acid bacteria can also improve the memory ability of the aged fruit flies, the above-mentioned olfactory memory assay was further carried out on the aged fruit flies at 21 days after emergence. The aged fruit flies were analyzed for changes in olfactory learning and memory ability after feeding lactic acid bacteria for 5 days compared with those without feeding lactic acid bacteria. The results of 3-minute memory assay showed that the memory ability of the aged fruit flies without feeding lactic acid bacteria declined compared with the young fruit flies (FIG. 4A). Moreover, the memory ability of the aged fruit flies fed GMNL-185 or GMNL-680 alone was not improved significantly (FIG. 4A). However, the memory ability of the aged fruit flies fed the composition of GMNL-185 and GMNL-680 (i.e., the probiotic composition of the present disclosure, with the ratio of 1:1) was significantly improved, which could return to the same short-term (3 minutes) memory ability as the young fruit flies (FIG. 4A). It should be noted that both the aged fruit flies (control group, aged) and the young fruit flies (control group, young) indicated that the fruit flies were not fed any lactic acid bacteria. In addition, the long-term (1 hour) memory ability of the aged fruit flies fed single lactic acid bacteria or fed the lactic acid bacteria composition (i.e., the probiotic composition of the present disclosure, with a ratio of 1:1) was not significantly improved (FIG. 4B), in which the control group represents the aged fruit flies without feeding lactic acid bacteria.

Figure 5A:
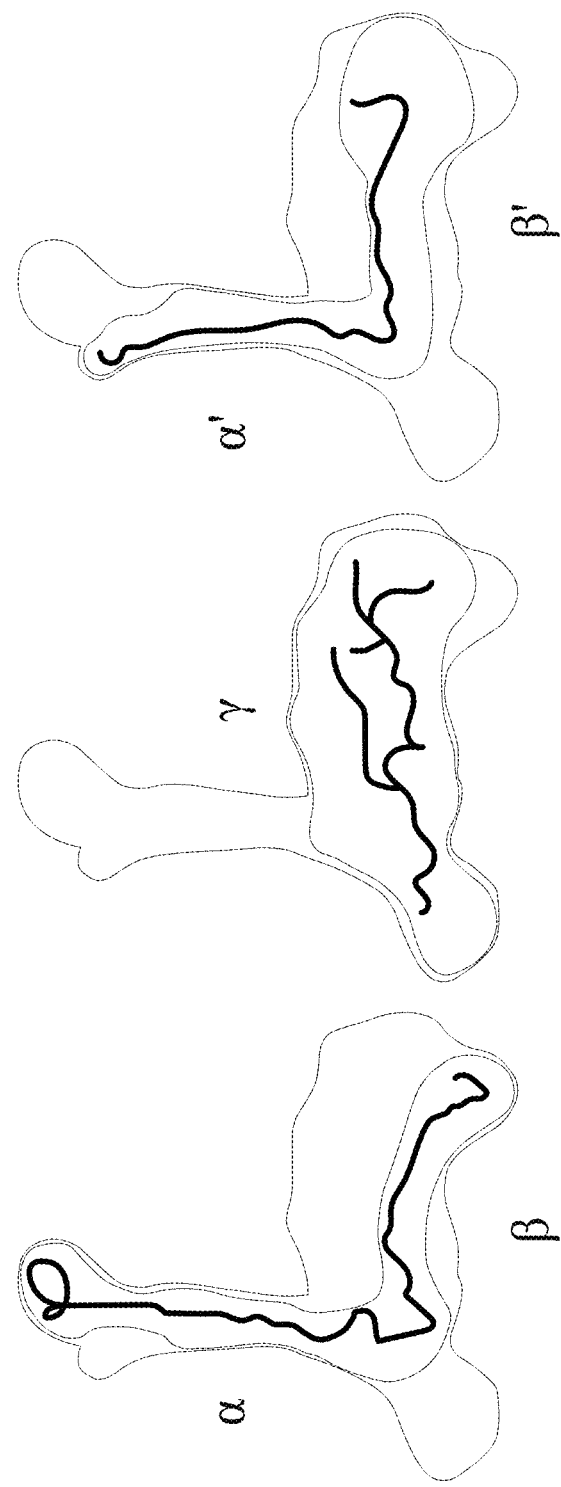
FIG. 5A to FIG. 5F respectively show analysis of memory traces of young fruit flies after feeding a combination of GMNL-185 and GMNL-680 for 5 days.
Figure 5B:
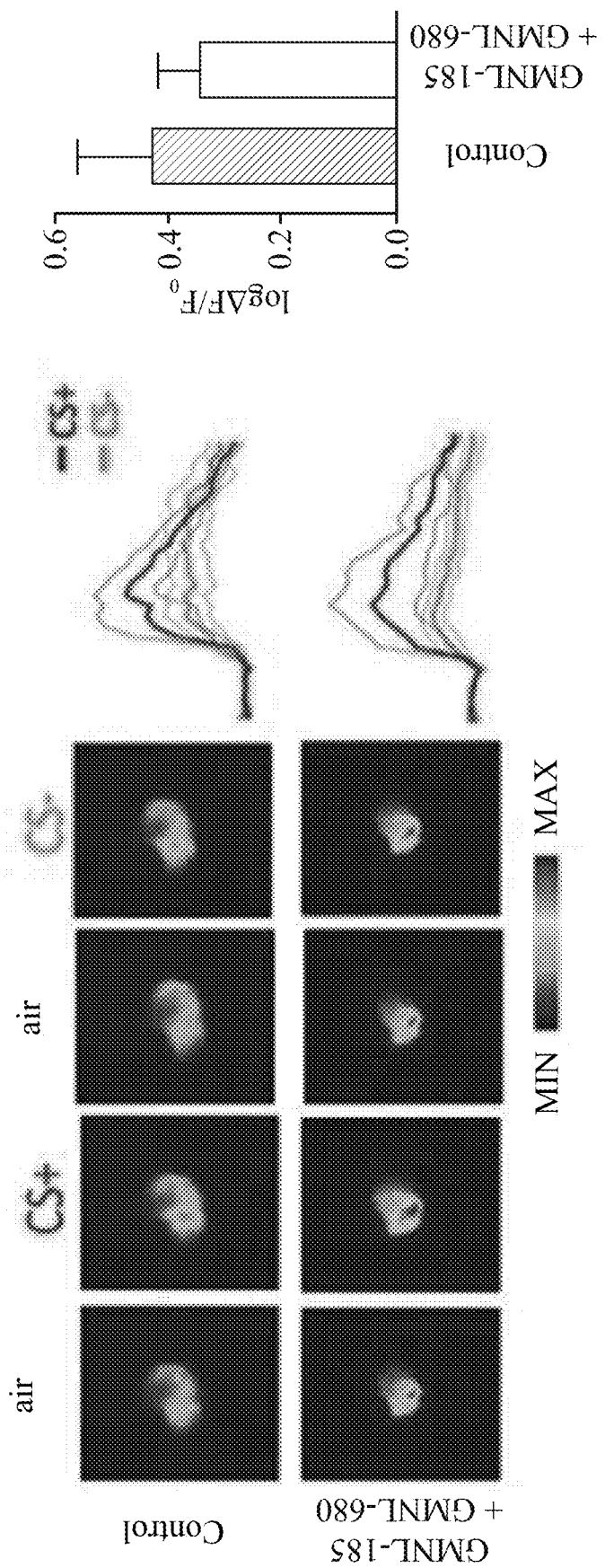
Figure 5C:
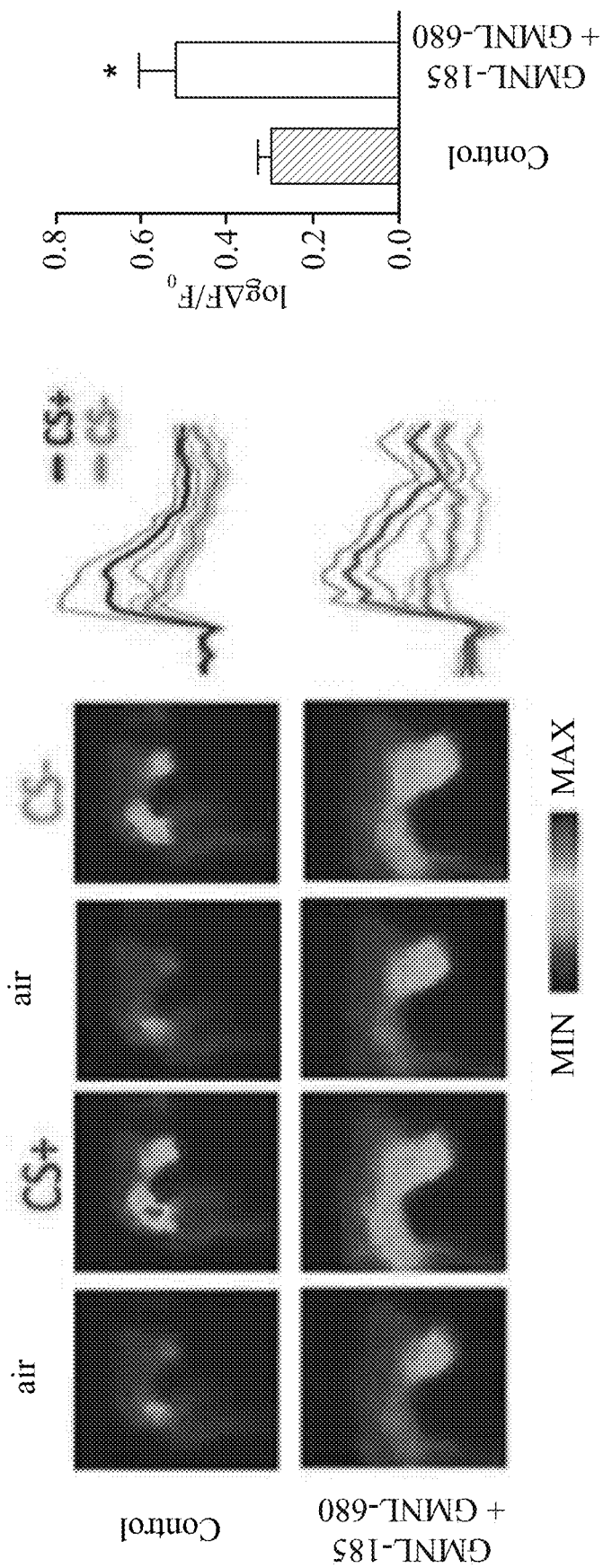
Figure 5D:
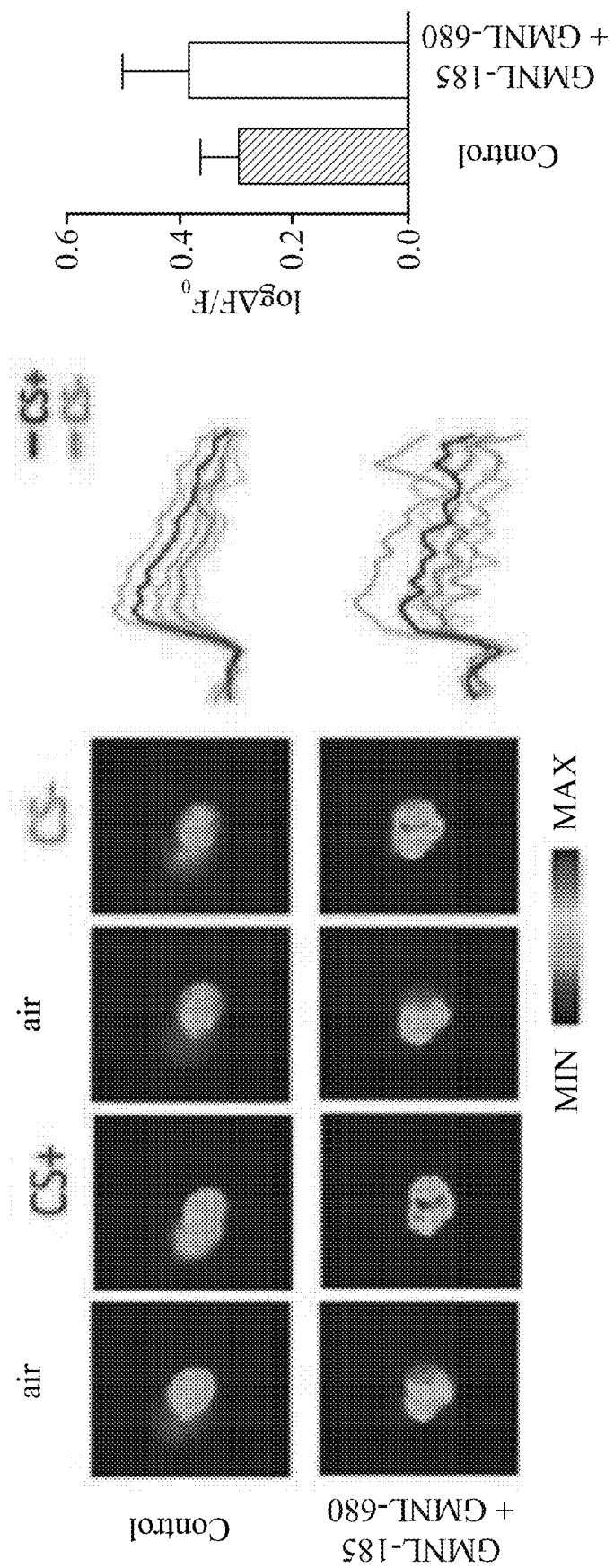
Figure 5E:
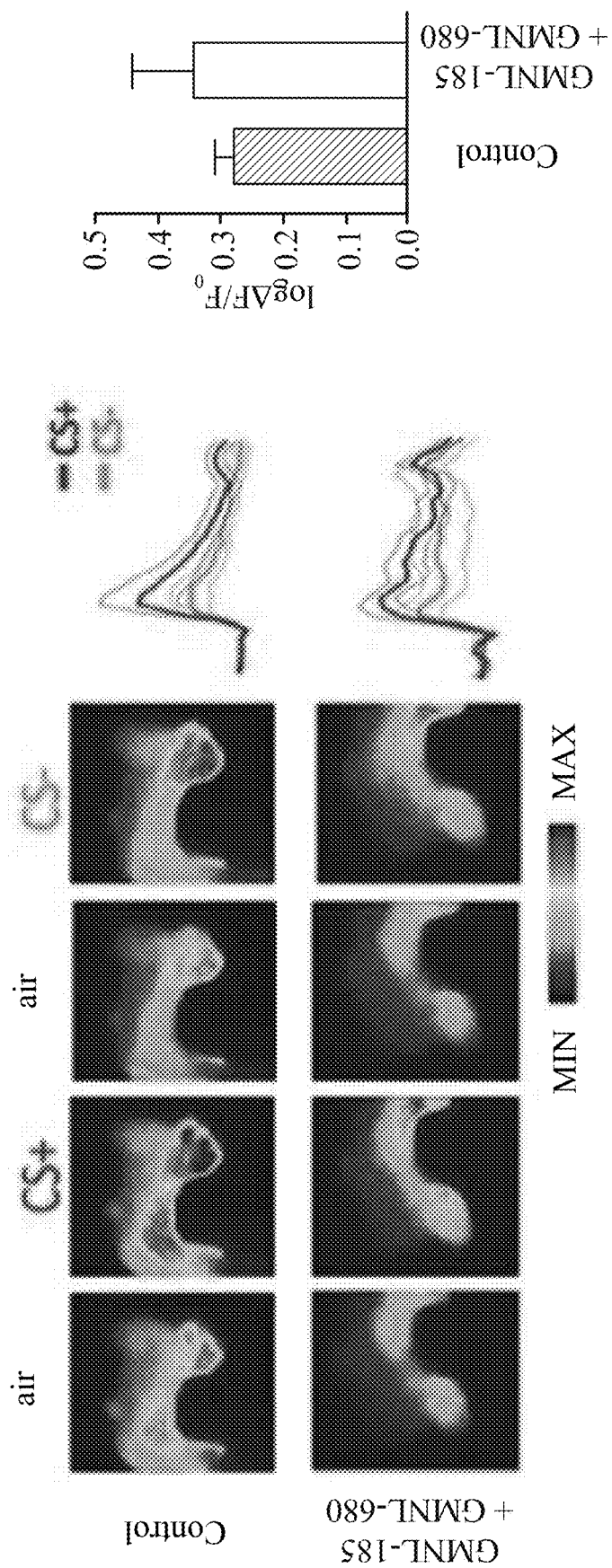
Figure 5F:
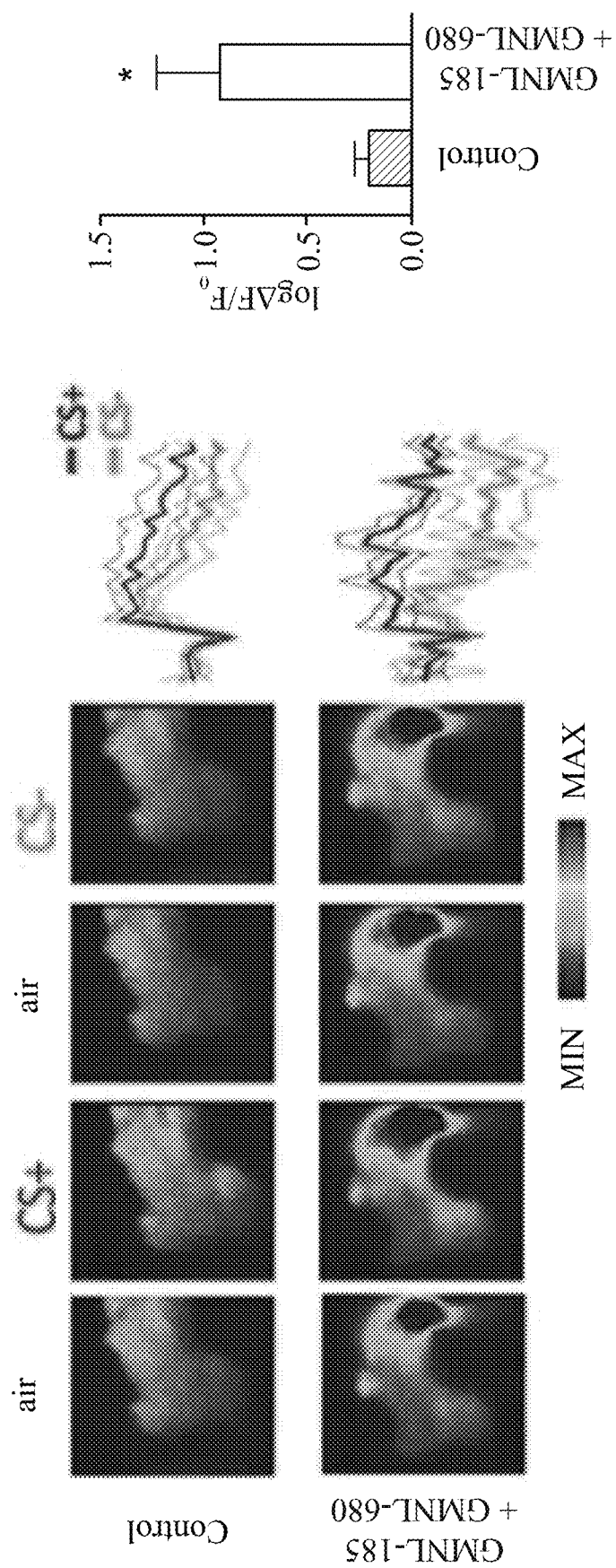
Figure 6A:
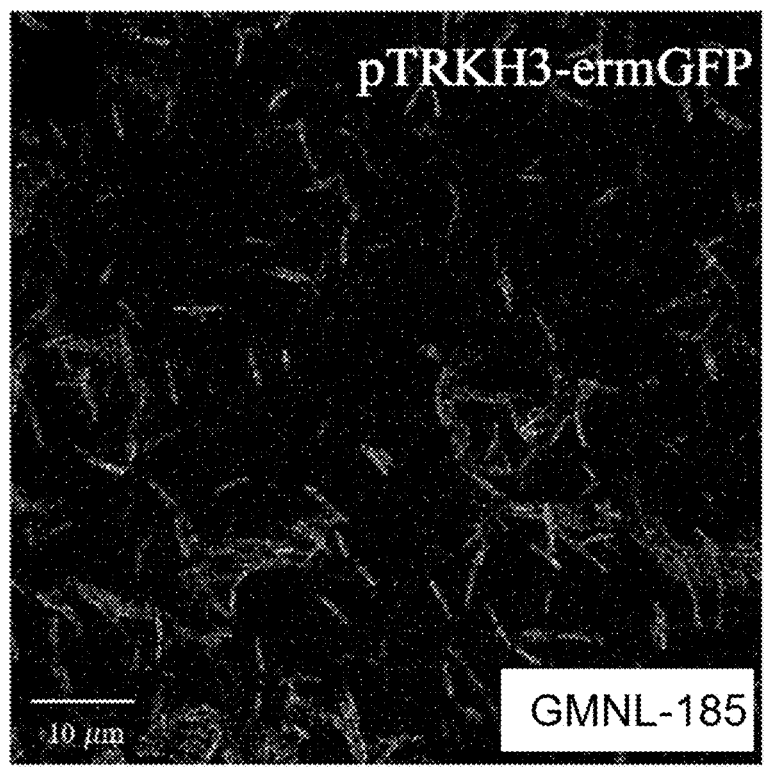
FIG. 6A to FIG. 6D are confocal microscopy images of expression of fluorescent proteins in GMNL-185 and GMNL-680, respectively.
Figure 6B:
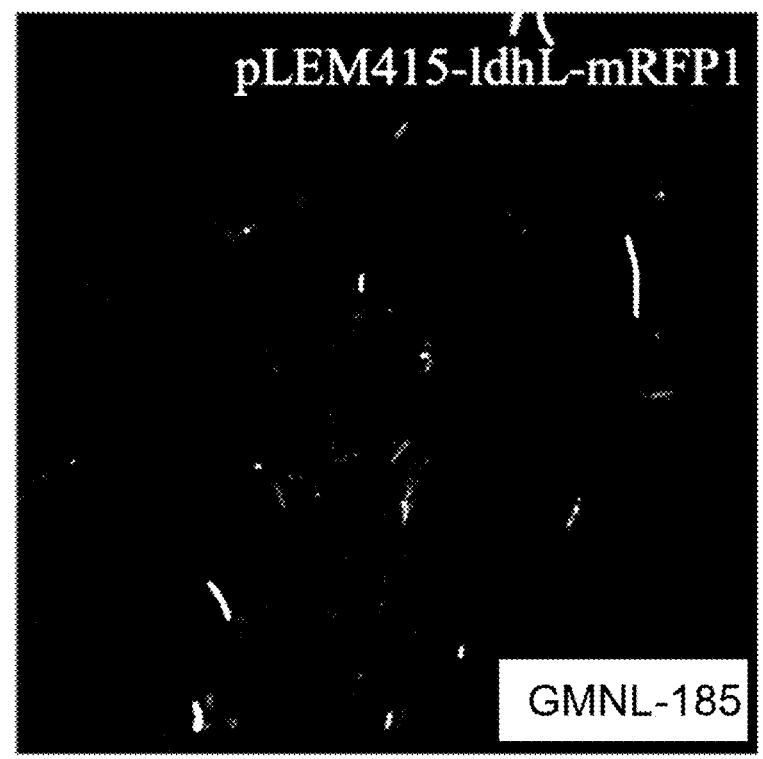
Figure 6C:
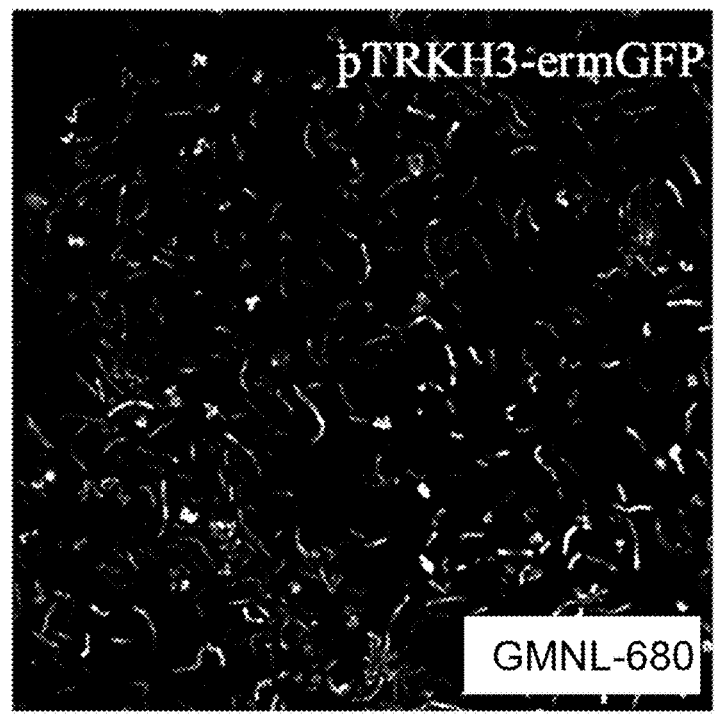
Figure 6D:
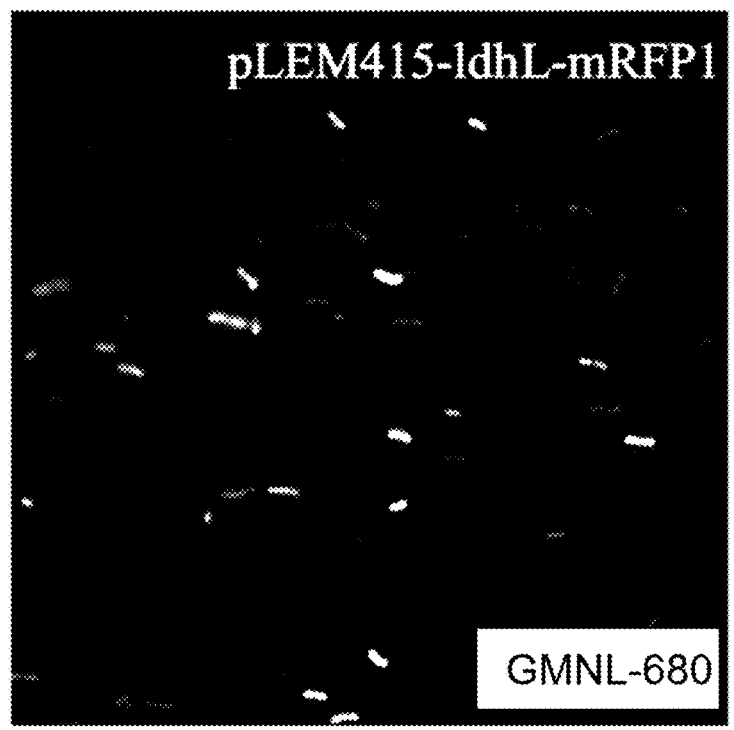

Observation of Changes in Activity of Mushroom Body Neurons of Fruit Flies After Feeding Lactic Acid Bacteria In order to understand whether the brain neural activity of the young fruit flies after feeding the composition of GMNL-185 and GMNL-680 (i.e., the probiotic composition of the present disclosure, with a ratio of 1:1) for 5 days was significantly changed compared with the group without feeding lactic acid bacteria, UAS-GCaMP was driven through R13F02-GAL4 by the GAL4/UAS system to express in mushroom body neurons, wherein the mushroom body is the main center of learning and memory in the brain of the fruit fly, so that the image of calcium ion changes in the mushroom body neurons of the live fruit flies could be observed, so as to know the activity changes of the neurons. The mushroom body of the fruit fly consists of three types of neurons, $\alpha/\beta$, $\alpha'/\beta'$, and $\gamma$. The axons of these neurons extend towards the front of the brain and branch into five different lobes (FIG. 5A), i.e., the $\alpha$-lobe (FIG. 5B), the $\beta$-lobe (FIG. 5C), the $\alpha'$-lobe (FIG. 5D), the $\beta'$-lobe (FIG. 5E), and the $\gamma$-lobe (FIG. 5F). A group of fruit flies exposed to an odor while receiving shocks (CS+) was compared with another group of fruit flies exposed to an odor without shocks (CS−). After olfactory learning, when the group exposed to the odor with shocks (CS+) again just like at the beginning of learning, compared with the group exposed to the odor without shocks, there were different calcium ion imaging responses in different lobes of the mushroom body, which is called a memory trace. The memory trace represents that when the fruit flies were exposed to CS+, the specific neurons were in the strong activation state, which can be used as an observation way of memory. It was found that the $\beta$-lobes (FIG. 5C) and the $\gamma$ lobes (FIG. 5F) of the mushroom bodies of the fruit flies fed the composition of GMNL-185 and GMNL-680 (i.e., the probiotic composition of the present disclosure, with a ratio of 1:1) for 5 days showed an obvious trend of enhanced memory traces compared with the group without feeding the composition of GMNL-185 and GMNL-680. The above results confirm that when the fruit flies were fed the composition of GMNL-185 and GMNL-680 (i.e., the probiotic composition of the present disclosure), the neural activity of specific neural regions in the brain and the intensity of memory traces could be changed, thereby improving memory ability.

Lactic Acid Bacteria Exhibited Fluorescent Proteins, and could Colonize and Grow Within Fruit Fly Guts The fluorescent protein gene plastmids pTRKH3-ermGFP (green fluorescence) or pLEM415-IdhL-mRFP1 (red fluorescence) were respectively introduced into lactic acid bacteria and observed by a confocal microscopy. As shown in FIG. 6A to FIG. 6D, GMNL-185 can exhibit green fluorescence (FIG. 6A) and red fluorescence (FIG. 6B) respectively. GMNL-680 can also exhibit green fluorescence (FIG. 6C) and red fluorescence (FIG. 6D) respectively.

Figure 7A:
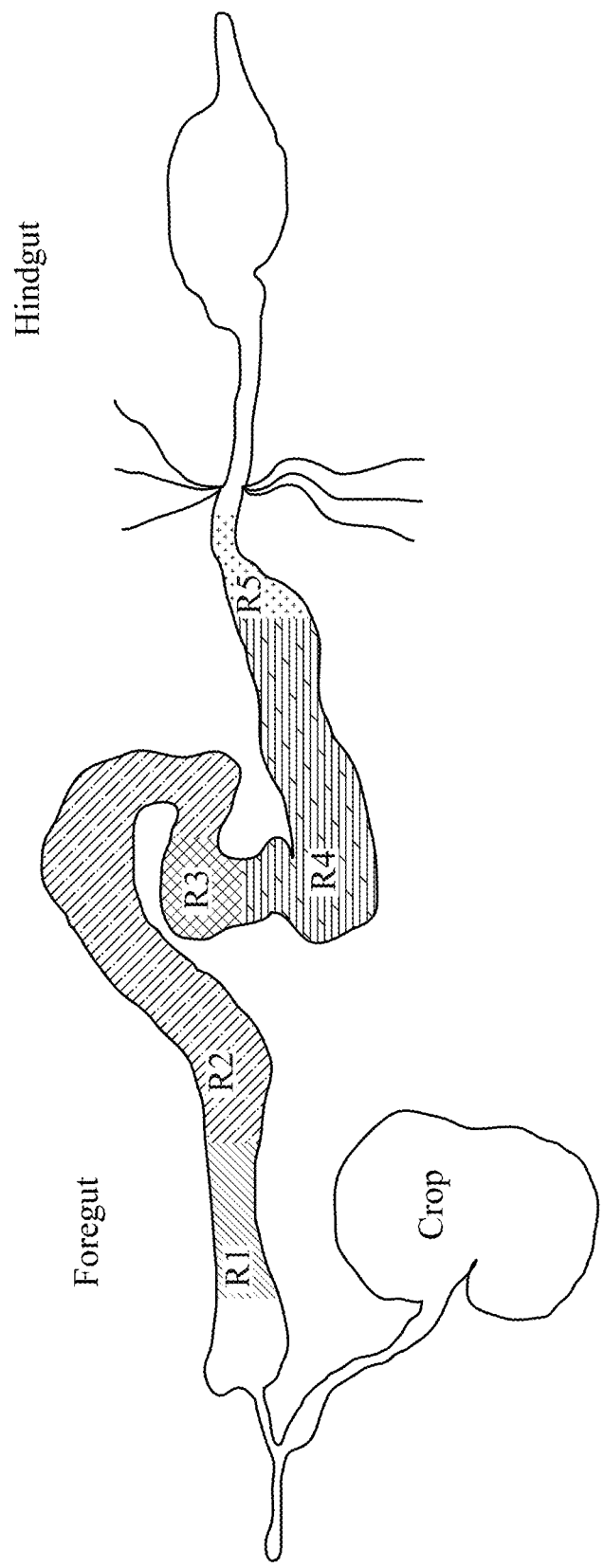
FIG. 7A to FIG. 7G respectively show that after feeding the GMNL-185 and GMNL-680 expressing fluorescent proteins, distributions of the GMNL-185 and GMNL-680 in guts of the fruit flies.
Figure 7B:
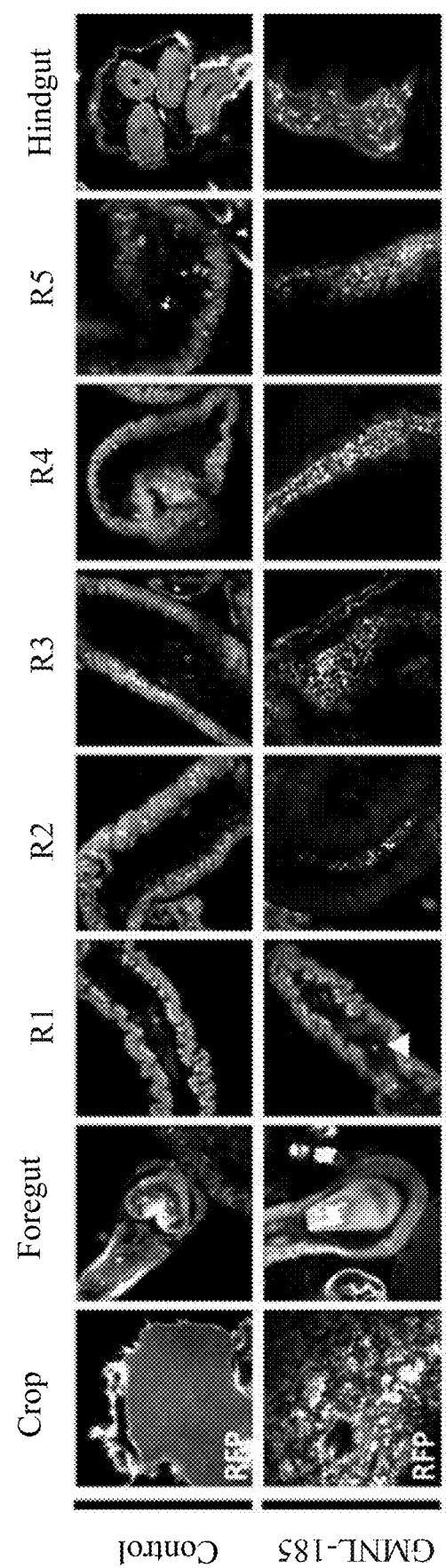
Figure 7C:
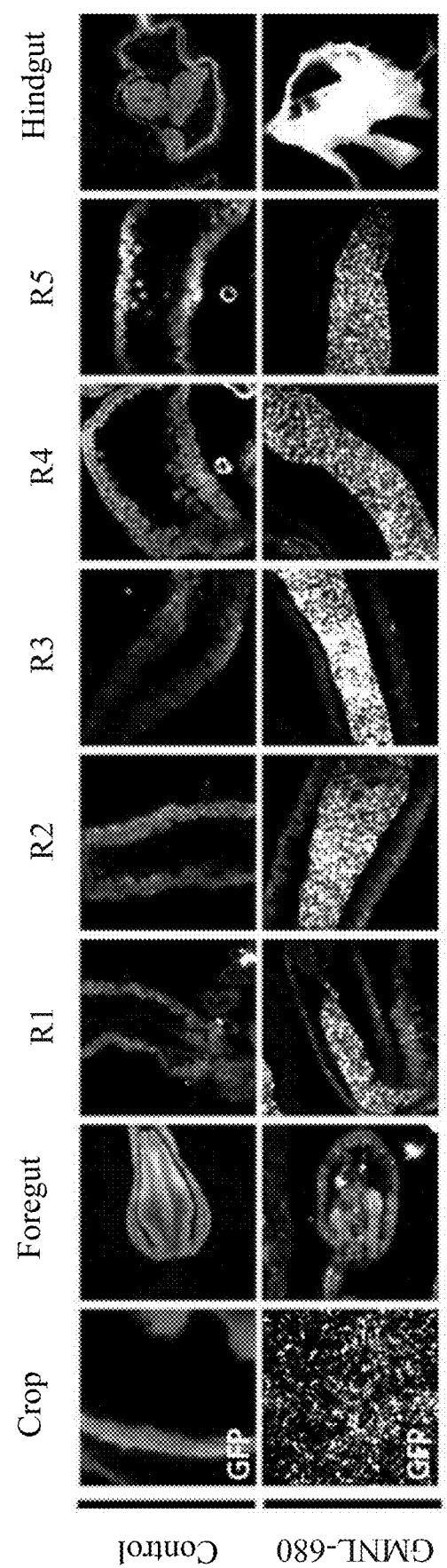
Figure 7D:
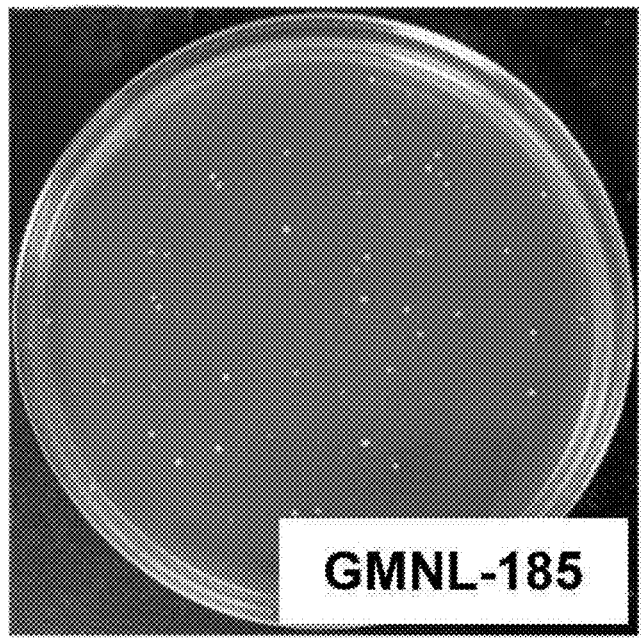
Figure 7E:
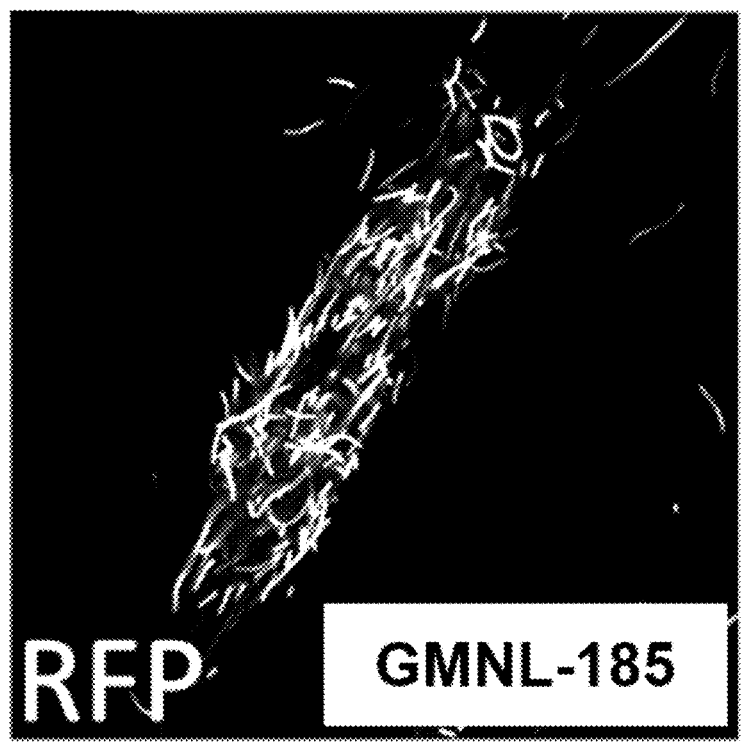
Figure 7F:
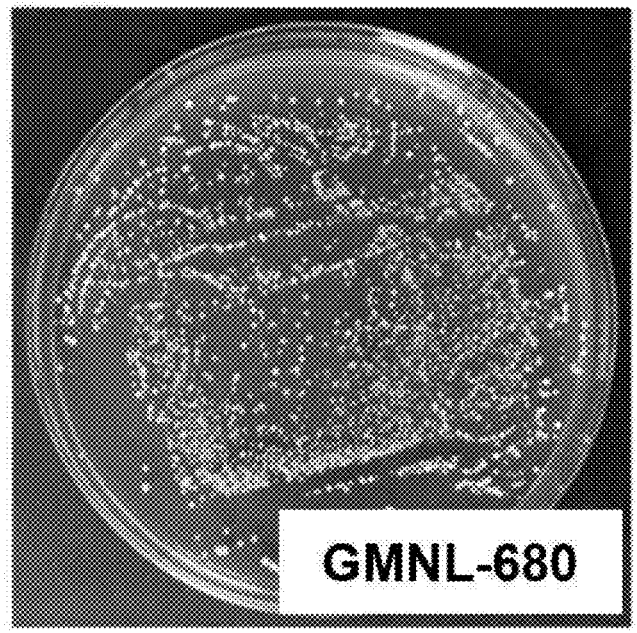
Figure 7G:
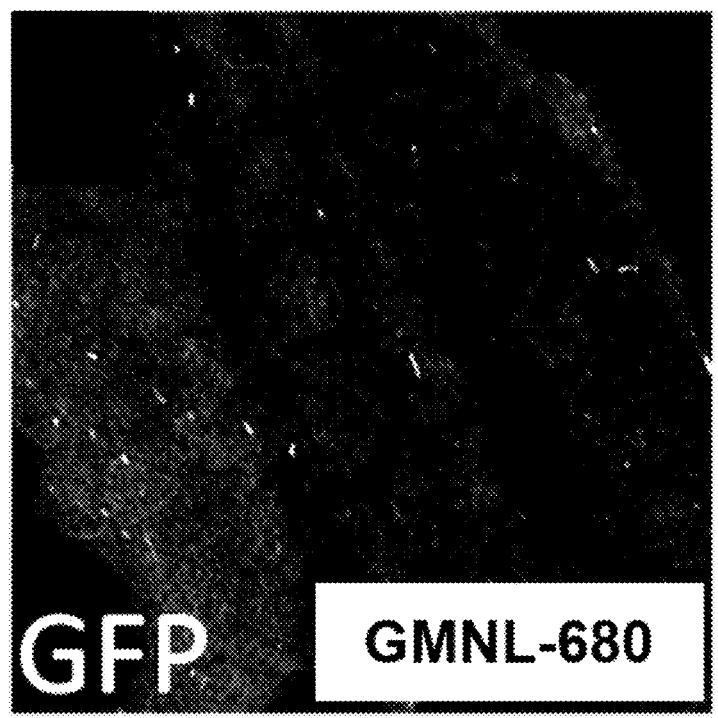

GMNL-185 with red fluorescent protein gene and GMNL-680 with green fluorescent protein gene were mixed in the *Drosophila* growth medium and fed to the fruit flies. After continuous feeding for 5 days, the guts of the fruit flies were dissected, and fluorescence performances in the guts of the fruit flies after feeding the lactic acid bacteria medium were observed by the confocal microscopy. A schematic diagram of different regions of a gut of a fruit fly is shown in FIG. 7A, including the crop, foregut, R1, R2, R3, R4, R5, and hindgut regions. It was found that no dotted red fluorescence was detected in the gut lumens of the fruit flies without feeding lactic acid bacteria (control group), while in the group of those fed GMNL-185 with red fluorescent protein, there was an obvious red dotted fluorescence expression in each gut region (FIG. 7B). Similarly, no dotted green fluorescence was detected in the gut lumens of the fruit flies without feeding lactic acid bacteria (control group), while in the group of those fed GMNL-680 with green fluorescent protein, there was an obvious green dotted fluorescence expression in each gut region (FIG. 7C). Further, the gastrointestinal tracts of the fruit flies fed lactic acid bacteria were cut off, ground, homogenized, and spread on the MRS agar plates for the culture of *lactobacilli*. The culture results of the MRS agar plates are shown in FIG. 7D and FIG. 7F. The colonies on the MRS agar plates were picked and spread on slides, and then the fluorescence signals of bacteria were observed by the confocal microscopy. The results showed that lactic acid bacteria isolated from the guts of the fruit flies would respectively exhibit red fluorescence (FIG. 7E) and green fluorescence (FIG. 7G). The above results showed that after the fruit flies fed the GMNL-185 and GMNL-680, the GMNL-185 and GMNL-680 could colonize in the gut as living bacteria.

Effect of Lactic Acid Bacteria on Gut Microbiome of Fruit Flies

Figure 8A:
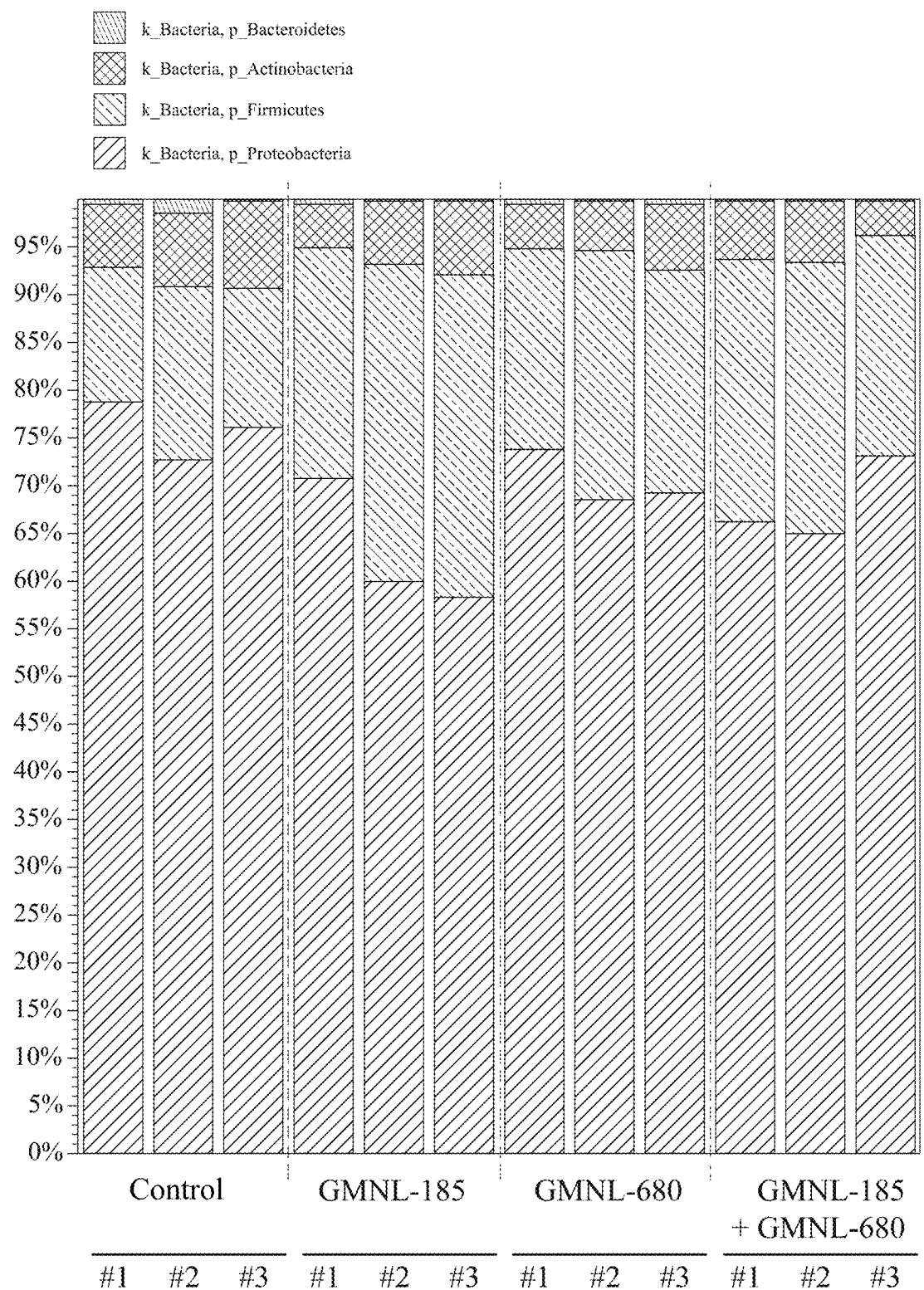
Figure 8B:
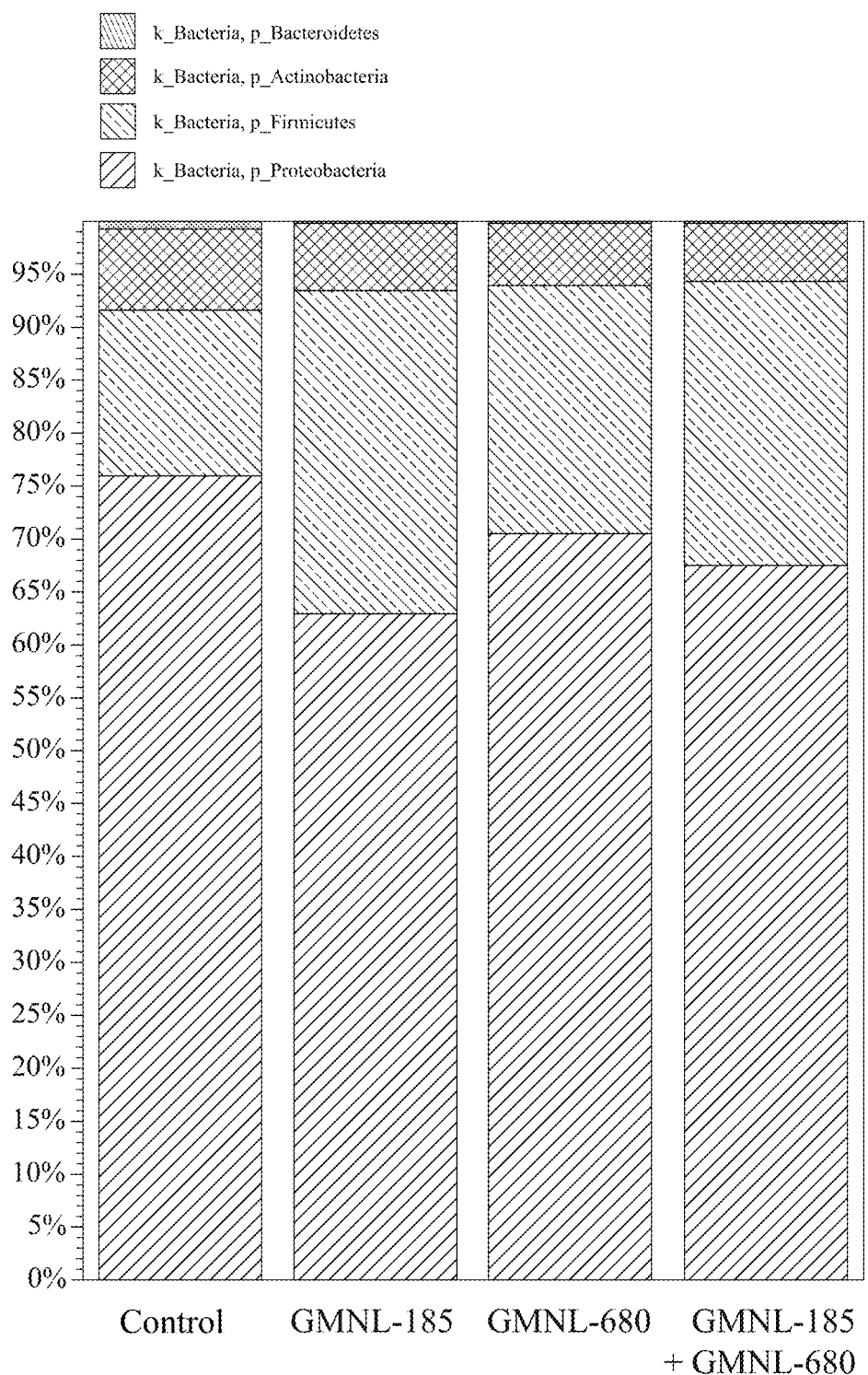
Figure 9A:
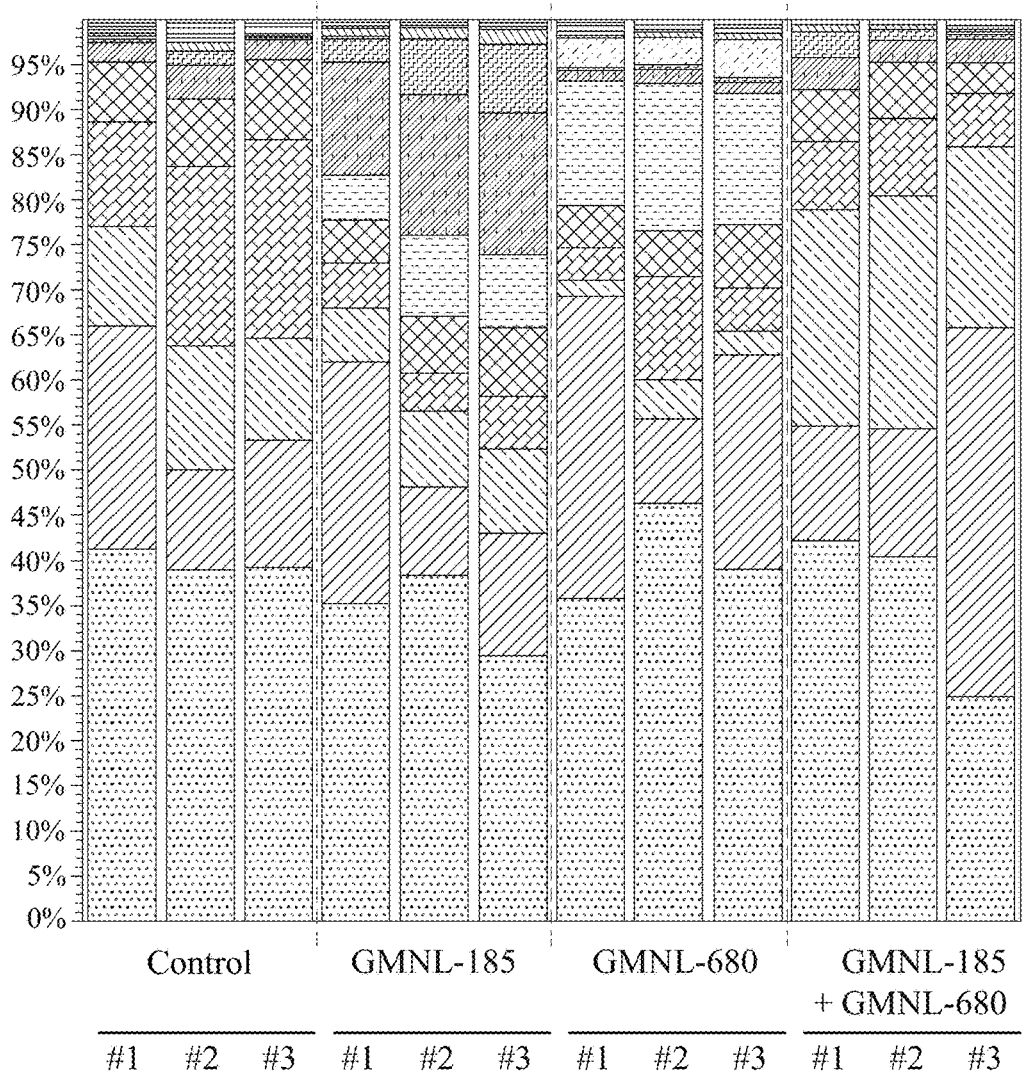
Figure 9B:
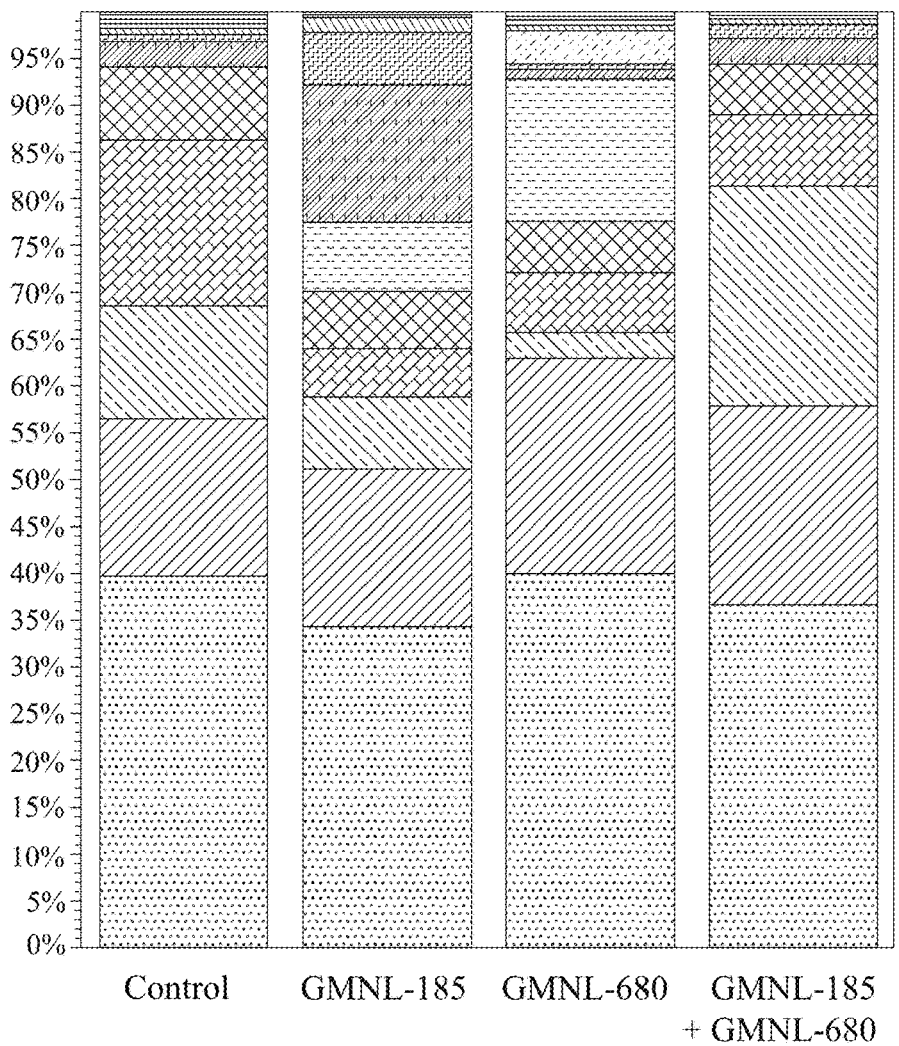

High-throughput sequencing technologies and bioinformatics analyses were used to compare changes in the gut microbiota of young fruit flies at 7 days after emergence after feeding lactic acid bacteria for continuous 5 days with that of a group without feeding lactic acid bacteria, and phylum OUTs and genus OUTs thereof were made into bar charts (FIG. 8A, FIG. 8B, FIG. 9A, and FIG. 9B). FIG. 8*a* and FIG. 9A respectively show the individual changes in the distribution of the phylum and genus in the gut microbiome of fruit flies in each group, wherein #1-#3 refer to the guts of fruit flies in 3 tubes per group, and each tube was combined with the guts of 15 fruit flies. FIG. 8B and FIG. 9B respectively show average distributions of the phylum and genus in the gut microbiome of fruit flies in each group (the average of tubes #1-#3 in each group). The results show that the gut microbiome of fruit flies could be changed by taking single and combined lactic acid bacteria strains. Pertaining to the phylum, refer to FIG. 8A and FIG. 8B, the relative abundance of Firmicutes related to memory ability in the guts of fruit flies was increased after feeding lactic acid bacteria. Pertaining to the genus, refer to FIG. 9A and FIG. 9B, the relative abundance of *Lactobacillus* in the guts of fruit flies was increased after feeding GMNL-185, and the relative abundance of *Pediococcus* was most significantly increased after feeding the combination of GMNL-185 and GMNL-680. It is known that *Lactobacillus* and *Pediococcus* are related to memory improvement.

Figure 10:
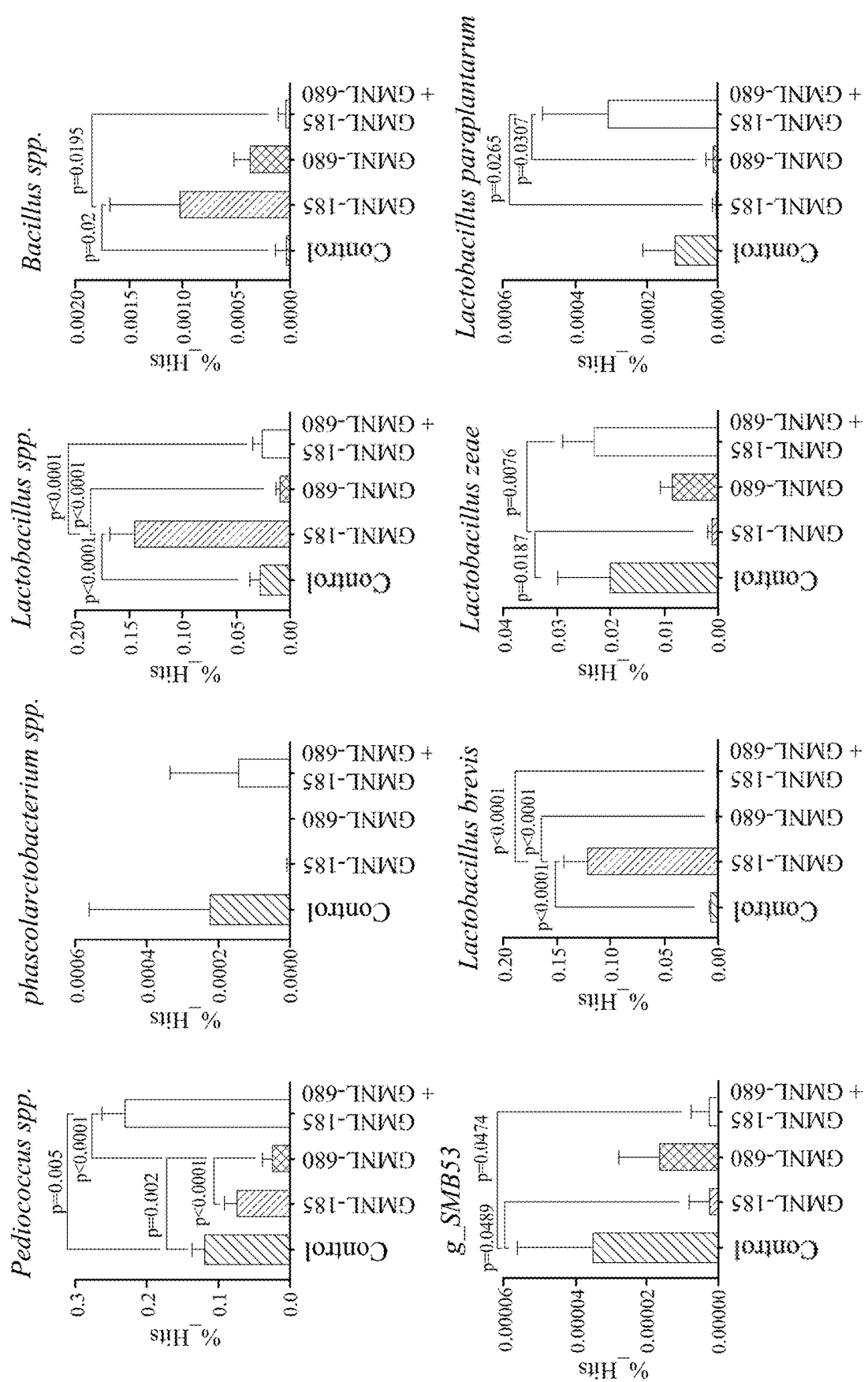
FIG. 10 shows changes of gut microbiota of fruit flies after feeding GMNL-185, GMNL-680, and a combination of GMNL-185 and GMNL-680.

Refer to FIG. 10. The "% of Hits" refers to the content, which means a number of bacteria detected by the instrument during the microbiome analysis. The higher the "% of Hits" is, the more a total number of a certain bacteria is. In other words, the higher a value is, the higher the proportion of the bacteria is. The statistical difference (P<0.05) represents the part with significant change. In the group of GMNL-185, the numbers of *Lactobacillus, Bacillus* and *Lactobacillus* brevis were significantly higher than those of other groups. In the group of the composition of GMNL-185 and GMNL-680, the numbers of *Lactobacillaceae, Pediococcus, Lactobacillus zeae,* and *Lactobacillus paraplantarum*, which all belong to *Lactobacillaceae*, were significantly higher than those of other groups. As mentioned above, the relative abundance of Firmicutes, *Lactobacillus* and *Pediococcus* in the guts of fruit flies could be increased after single or compound lactic acid bacteria (i.e., the combination of GMNL-185 and GMNL-680) were administrated. Firmicutes, *Lactobacillus*, and *Pediococcus* are known that can improve memory ability.

To sum up, after the probiotic composition of the present disclosure was fed, the probiotic composition could colonize and grow within the gut of the individual. Moreover, the relative abundance of Firmicutes, *Lactobacillus*, and *Pediococcus* in the gut could be changed by the probiotic composition, thereby changing the neural activity of specific neural regions in the brain and strength of memory traces, so as to achieve the effect of enhancing memory and learning ability of the individual.

While the preferred embodiments of the present disclosure have been described above, it will be recognized and understood that various changes and modifications can be made, and the appended claims are intended to cover all such changes and modifications which may fall within the spirit and scope of the present disclosure.

What is claimed is:

1. A method of improving memory and learning ability, comprising: administering a probiotic composition to a subject who needs to improve memory or learning ability, wherein the probiotic composition includes *Lactobacillus acidophilus* GMNL-185 and *Lactobacillus rhamnosus* GMNL-680, wherein the *Lactobacillus acidophilus* GMNL-185 was deposited in the China Center for Type Culture Collection in Wuhan, China on Nov. 3, 2017 under an accession number CCTCC NO. M 2017764, and the *Lactobacillus rhamnosus* GMNL-680 was deposited in the China Center for Type Culture Collection in Wuhan, China on Nov. 3, 2017 under an accession number CCTCC NO. M 2017766, and a ratio of a number of bacteria of the *Lactobacillus acidophilus* GMNL-185 to a number of bacteria of the *Lactobacillus rhamnosus* GMNL-680 is 1:1.

* * * * *

SEQUENCE LISTING

```
Sequence total quantity: 4
SEQ ID NO: 1            moltype = DNA  length = 20
FEATURE                 Location/Qualifiers
misc_feature            1..20
                        note = PAF primer
source                  1..20
                        mol_type = other DNA
                        organism = synthetic construct
SEQUENCE: 1
agagtttgat cctggctcag                                                   20

SEQ ID NO: 2            moltype = DNA  length = 18
FEATURE                 Location/Qualifiers
misc_feature            1..18
                        note = 536R primer
source                  1..18
                        mol_type = other DNA
```

```
                        organism = synthetic construct
SEQUENCE: 2
gtattaccgc ggctgctg                                                  18

SEQ ID NO: 3            moltype = DNA  length = 506
FEATURE                 Location/Qualifiers
misc_feature            1..506
                        note = Partial sequence of 16S rDNA of Lactobacillus
                         acidophilus GMNL-185
source                  1..506
                        mol_type = other DNA
                        organism = synthetic construct
SEQUENCE: 3
ctgcggtgct atacatgcaa gtcgagcgag ctgaaccaac agattcactt cggtgatgac   60
gttgggaacg cgagcggcgg atgggtgagt aacacgtggg gaacctgccc catagtctgg  120
gataccactt ggaaacaggt gctaataccg gataagaaag cagatcgcat gatcagctta  180
taaaaggcgg cgtaagctgt cgctatggga tggccccgcg gtgcattagc tagttggtag  240
ggtaacggcc taccaaggca atgatgcata gccgagttga gagactgatc ggccacattg  300
ggactgagac acggcccaaa ctcctacggg aggcagcagt agggaatctt ccacaatgga  360
cgaaagtctg atggagcaac gccgcgtgag tgaagaaggt tttcggatcg taaagctctg  420
ttgttggtga agaaggatag aggtagtaac tggcctttat ttgacggtaa tcaaccagaa  480
agtcacggct aactacgtgc cagacg                                        506

SEQ ID NO: 4            moltype = DNA  length = 526
FEATURE                 Location/Qualifiers
misc_feature            1..526
                        note = Partial sequence of 16S rDNA of Lactobacillus
                         rhamnosus GMNL-680
source                  1..526
                        mol_type = other DNA
                        organism = synthetic construct
SEQUENCE: 4
caggggtgcc taatacatgc aagtcgaacg agttctgatt attgaaaggg tgcttgcatc   60
ttgatttaat tttgaacgag tggcggacgg gtgagtaaca cgtgggtaac ctgcccttaa  120
gtggggata acatttggaa acagatgcta ataccgcata aatccaagaa ccgcatggtt  180
cttggctgaa agatgcgta agctatcgct tttggatgga cccgcggcgt attagctagt  240
tggtgaggta acggctcacc aaggcaatga tacgtagccg aactgagagg ttgatcggcc  300
acattgggac tgagacacgg cccaaactcc tacgggaggc agcagtaggg aatcttccac  360
aatggacgca agtctgatgg agcaacgccg cgtgagtgaa gaaggctttc gggtcgtaaa  420
actctgttgt tggagaagaa tggtcggcag agtaactgtt gtcggcgtga cggtatccaa  480
ccagaaagcc acggctaact acgtgccagc agccgggta atacaa                  526
```